US007459165B2

(12) United States Patent
Charland et al.

(10) Patent No.: US 7,459,165 B2
(45) Date of Patent: Dec. 2, 2008

(54) **POLYPEPTIDES OF *PSEUDOMONAS AERUGINOSA***

(75) Inventors: Nathalie Charland, Breakeyville (CA); Josee Hamel, Sillery (CA); Bernard Brodeur, Sillery (CA); Denis Martin, St-Augustin-de-Desmaures (CA); Isabelle Charlebois, St-Nicolas (CA); Diane Bussiere, St-Nicolas (CA)

(73) Assignee: ID Biomedical Corporation, Laval (CA)

( * ) Notice: Subject to any disclaimer, the term of this patent is extended or adjusted under 35 U.S.C. 154(b) by 0 days.

(21) Appl. No.: 10/495,455

(22) PCT Filed: Nov. 13, 2002

(86) PCT No.: PCT/CA02/01740

§ 371 (c)(1),
(2), (4) Date: Nov. 17, 2004

(87) PCT Pub. No.: WO03/042240

PCT Pub. Date: May 22, 2003

(65) Prior Publication Data

US 2005/0107597 A1     May 19, 2005

Related U.S. Application Data

(60) Provisional application No. 60/331,221, filed on Nov. 13, 2001.

(51) Int. Cl.
*A61K 39/104* (2006.01)
*A61K 39/02* (2006.01)
*C07K 14/00* (2006.01)
*C07H 21/04* (2006.01)
*C12P 21/04* (2006.01)

(52) U.S. Cl. ............... 424/260.1; 424/190.1; 530/300; 530/350; 435/69.1; 435/69.7; 435/252.3; 435/320.1; 536/23.4; 536/23.7; 514/44; 514/459

(58) Field of Classification Search ............... 435/69.1, 435/69.7, 252.3, 320.1; 424/260.1, 190, 424/190.1; 514/44, 459; 536/23.4, 23.7; 530/300, 350

See application file for complete search history.

(56) References Cited

U.S. PATENT DOCUMENTS 4,338,397 A    7/1982  Gilbert et al. ............... 435/68
4,425,437 A    1/1984  Riggs ............... 435/317
4,431,739 A    2/1984  Riggs ............... 435/253
6,551,795 B1 * 4/2003  Rubenfield et al. ......... 435/69.1

FOREIGN PATENT DOCUMENTS

| EP | 0 297 291 | 10/1993 |
| EP | 0 717 106 | 3/2000 |
| WO | WO 99/57142 | 11/1999 |
| WO | WO 01/02577 | 1/2001 |
| WO | WO 01/40473 | 6/2001 |
| WO | WO 02/064161 | 8/2002 |

OTHER PUBLICATIONS

Rudinger et al, in "Peptide Hormones", edited by Parsons, J.A., University Park Press, Jun. 1976.*
Burgess et al., The Journal of Cell Biology, 111:2129-2138, 1990.*
Lazar et al., Molecular and Cellular Biology, 8(3): 1247-1252, 1988; Jobling et al. (Mol. Microbiol. 1991, 5(7): 1755-67).*
Database: PIR_80, Accession No. F83148.*
Riffkin et al 1995, Gene 167: 279-283.*
Blackburn, N.T. et al., "Characterization of Soluble and Membrane-Bound Family 3 Lytic Transglycosylases from *Pseudomonas aeruginosa*," *Biochemistry* 41:1001-1013, 2002.
Gregoriadis, G., "Immunological adjuvants: a role for liposomes," *Immunology Today* 11(3):89-97, 1990.
Holder, I.A., "*Pseudomonas* lVaccination and Immunotherapy," *J. Burn Care Rehabil.* 22(5):311-320, 2001.
Jobling, M.G. et al., "Analysis of structure and function of the B subunit of cholera toxin by the use of site-directed mutagenesis," *Molecular Microbiology*, 5(7):1755-1767, 1991.
Stanislavsky, E.S. et al., "," *FEMS Microbiol. Rev.*, 21(3):243-277, 1997.
Stover, C.K. et al., "Complete Genome Sequence of *Pseudomonas aeruginosa* PA01, an Opportunistic Pathogen," *Nature, Macmillan Journals Ltd.*, London, GB, 406(6799):959-694, Aug. 31, 2000.
Database Accession No. Q9HX28.
Database Accession No. AE004817.
Jameson and Wolf. "The antigenic index: a novel algorithm for predicting antigenic determinants," Computer Application Bioscience, 4(1):181-186, 1988.
Wan et al., "Epitope Map for a Growth Hormone Receptor Agonist Monoclonal Antibody, MAb 263," Molecular Endocrinology, 17(11):2240-2250, 2003.

* cited by examiner

*Primary Examiner*—Shanon A. Foley
*Assistant Examiner*—Padma v Baskar
(74) *Attorney, Agent, or Firm*—Seed IP Law Group PLLC

(57) ABSTRACT

The present invention relates to polypeptides of *Pseudomonas aeruginosa* which may be used to prevent, diagnose and/or treat *Pseudomonas aeruginosa* infection.

10 Claims, 7 Drawing Sheets

Figure 1 (SEQ ID NO: 1)

```
   1 ATGCGTAACC CCGAACGATC CGCCCTGCTG AAGGTGAGCG GGCTGCTGGG CAGCACCGTC
  61 GTCGCCATGG GGCTTGGCCT CTCCAGCGCC TGCGCGCAGA AGAATCCGAC AGTCGAATAC
 121 AACCAGCCTG CCGCTCCCCT GCAGACCAAG GCGCCCTTCT CCGGCGCCGG CCCGGCCGCC
 181 TCGGTGCCCG CTGGCGCGCC GAACGAGGCC CAGCCTGGGC AAAGCTTCGA ACAGTGGCGC
 241 GACGCCTTCC GTCAACAGGC GCTGGCCGGT GGAATCGATG CGCAGACCTT CGATCGCGCC
 301 TTCGCCGGCG TCCAGCCCGA TCCCGCCGTG GTCGAAGCAG ACCGCAGCCA GCCGGAATTC
 361 ACCCGACCGG TATGGAAGTA CCTGGAAGGC GCCCTCGATC CGCTGCGCGT TCGCCAGGGC
 421 CAGGCGCGCC TGGCGCAGCA TGCGCGCATC CTCGGCGAAG TCGACGCGCG CTATGCGGTG
 481 GATGCGGATG CGGTGGTGGC GATCTGGGGC ATGGAGAGCA ACTACGGTTC GCACATGGGC
 541 AACAAGAACG TGATCCGCTC CCTGGCGACC CTCGCCTATG AAGGACGCCG CCCGGAATTC
 601 GCCCACGCCC AGTTGCTCGC CGCCCTGAAG ATTCTCCAGC ACGGCGACGT TCCGGCCTCC
 661 TTCATGATCG GCTCCTGGGC CGGCGCCATG GGCCAGACCC AGTTCATCCC GACCACCCAC
 721 AACCAGTATG CCGTGGACTT CGACGGCGAC GGCAAGCGTG ACATCTGGGG CTCGCCCGGC
 781 GACGCCCTGG CCTCCACCGC CAACTACCTG AAAGCCTCCG GCTGGATCGC CGGACAACCC
 841 TGGGGTTTCG AAGTCCGCCT GCCGGCAGGC TTCGACTATT CCCTGGCGGA ACTCACCATC
 901 CGCAAGCCCC TGGGCGAATG GCAAGGGATG GGCGTACAAG GCGTCAACGG CGGCCCCCTG
 961 CCCTCCGGAC TCTCCGGCGA ACAGGCCTCG CCTGCTGCTGC CGGCCGGGCA CCGGCGGCCCG
1021 GCCTTCCTGG TGCTGCACAA CTTCCGCGCC ATCCTCAAGT ACAACAACTC CAGCGCCTAC
1081 GCCCTGGCCG TCGGCCTGCT CGCCGACAGC TTCAAGGGCG GCGGCCGGAT AGTCGGCGCC
1141 TGGCCGCTGG AGGATGTTCC GCTGAGCCGC TCGCAGCGCA TCGAGCTGCA ACGGCAACTG
1201 GCCGCCCGCG GACACGATCC GGGCGCGGTG GATGGCATCA TCGGCGCCAA TACGCGCAAG
1261 GCGATCCGCG CCTGCCAGCA GGAGTTCGGC TGGCCGGCGG ACGGCTATCC GACCCCGGCG
1321 CTGCTCGACC GCCTGCGGAC GCCATAG
```

Figure 2 (SEQ ID NO: 2)

```
  1 MRNPERSALL KVSGLLGSTV VAMGLGLSSA CAQKNPTVEY NQPAAPLQTK APFSGAGPAA
 61 SVPAGAPNEA QPGQSFEQWR DAFRQQALAG GIDAQTFDRA FAGVQPDPAV VEADRSQPEF
121 TRPVWKYLEG ALDPLRVRQG QARLAQHARI LGEVDARYAV DADAVVAIWG MESNYGSHMG
181 NKNVIRSLAT LAYEGRRPEF AHAQLLAALK ILQHGDVPAS FMIGSWAGAM GQTQFIPTTH
241 NQYAVDFDGD GKRDIWGSPG DALASTANYL KASGWIAGQP WGFEVRLPAG FDYSLAELTI
301 RKPLGEWQGM GVQGVNGGPL PSGLSGEQAS LLLPAGHRGP AFLVLHNFRA ILKYNNSSAY
361 ALAVGLLADS FKGGGRIVGA WPLEDVPLSR SQRIELQRQL AARGHDPGAV DGIIGANTRK
421 AIRACQQEFG WPADGYPTPA LLDRLRTP*
```

Figure 3 (SEQ ID NO: 3)

```
  1 ATGAAACGTA TCCTGACCAG CGCCGCGCTG ATCGGTATGA CCACCCTGCT GGCCGCCTGC
 61 GGCTTCCAAC TGCGCGGCCT GGGCGATGCG CAATTCGCGC TCAAGGAAAT CGACGTGTCC
121 GCGCGCAACG CCTACGGCCC GACCGTGCGC GAACTGAAGG AAACCCTGGA AACAGCGGC
181 GTGAAGGTCA CCAGCAACGC GCCCTACCAC CTGGTGCTGG TCCGCGAGGA CAACCAGCAG
241 CGCACCGTCA GCTACACCGG TTCCGCGCGC GGCGCGGAGT TCGAGCTGAC CAACACGATC
301 AACTACGAGA TCGTCGGCGC CAACGACCTG GTCCTGATGA GCAACCAGGT ACAGGTGCAG
361 AAGGTCTACG TGCACGACGA AAACAACCTG ATCGGTTCCG ACCAGGAAGC CGCGCAGCTG
421 CGCAGCGAGA TGCGGCGCGA CCTGATCCAG CAGTTGTCCA TGCGCCTCCA GGCGCTGACC
481 CCGGCGCAAC TCGACGAAGC CCAGCGCCAG GCAGAAGCCA AGGCCAAGGC GGAAGCCGAA
541 GCCCTGCGCG CCGCCGACGA GGCGGAGCGC CAGCGCCGCG CCGCCGAGCC GCAGCAGTCG
601 CCGATCGAGT TCCCCACCCC GTGA
```

Figure 4 (SEQ ID NO: 4)

```
  1 MKRILTSAAL IGMTTLLAAC GFQLRGLGDA QFALKEIDVS ARNAYGPTVR ELKETLENSG
 61 VKVTSNAPYH LVLVREDNQQ RTVSYTGSAR GAEFELTNTI NYEIVGANDL VLMSNQVQVQ
121 KVYVHDENNL IGSDQEAAQL RSEMRRDLIQ QLSMRLQALT PAQLDEAQRQ AEAKAKAEAE
181 ALRAADEAER QRRAAEPQQS PIEFPTP*
```

Figure 5 (SEQ ID NO: 5)
```
   1 ATGGTGCAAT GGAAACACGC GGCGCTGCTC GCCCTGGCCC TGGCGGTCGT GGGTTGCAGC
  61 AGCAACAGCA AGAAGGAACT CCCGCCCGCC GAACTGACCG ACTTCAAAGA GGAAGTCGTG
 121 TTGAGCAAGC AGTGGAGCCG CTCGGTCGGT GATGGTCAGG GCGACCTGTA CAACCTGCTC
 181 GAACCGGCCG TCGATGGTTC CACCATCTAC GCCGCGTCCG CCGAAGGGCG GGTGATGGCG
 241 ATCCAGCGCG AGACCGGCGA CGTGCTCTGG AAGAAGGACC TGGAACGTCC GGTTTCCGGC
 301 GGTGTCGGCG TTGGCTACGG CCTGGTGCTG GTGGGTACCC TGCGCGGTGA CGTGATCGCC
 361 CTCGACGAAG CCACCGGCAA GAAGAAGTGG ACCAAGCGAG TCAACAGCGA AGTGCTGTCG
 421 GCGCCGGCCA CCAATGGCGA CGTGGTGGTG GTGCAGACCC AGGACGACAA GCTGATCGGC
 481 CTCGATGCGG CCAGCGGCGA CCAGCGCTGG ATCTACGAAA GCACCGTGCC GGTGCTGACC
 541 CTGCGCGGCA CCGGCGCGCC GCTGATTGCC GGCAACATGG CCCTGGCTGG CCTGGCCAGC
 601 GGCAAGGTAG TGGCGGTCGA CGTACAGCGC GGCCTGCCGA TCTGGGAGCA GCGGGTAGCG
 661 ATTCCCCAGG GGCGTTCCGA ACTGGATCGC GTGGTGGACA TCGACGGCGG CCTCCTGCTG
 721 TCCGGCGACA CCCTCTACGT GGTCAGCTAC CAGGGCCGTG CCGCGGCGCT GGACGTGAAC
 781 AGCGGCCGCC TGCTCTGGCA GCGCGAAGCG TCGAGCTACG TCGGCGTCGC CGAAGGCTTC
 841 GGCAATATCT ACGTCAGCCA GGCCAGCGGT TCGGTGGAAG GCCTGGACTC GCGCGGCGCT
 901 TCTTCGCTGT GGAACAACGA CGCCCTGGCG CGTCGCCAAC TGTCGGCTCC GGCGGTGTTC
 961 TCCAGCAACG TGGTGGTCGG CGACCTGGAA GGCTACGTGC ACCTGCTGAG CCAGGTGGAC
1021 GGTCGCTTCG TCGGTCGCGA GCGGGTCGAC AGCGATGGCG TGCGGGTTCG TCCGCTGGTG
1081 GTCGGGAGCT GGATGTACGT GTTCGGCAAC GGTGGCAAGC TCGTCGCCTA CACCATCCGC
1141 TAG
```

Figure 6 (SEQ ID NO: 6)
```
   1 MVQWKHAALL ALALAVVGCS SNSKKELPPA ELTDFKEEVV LSKQWSRSVG DGQGDLYNLL
  61 EPAVDGSTIY AASAEGRVMA IQRETGDVLW KKDLERPVSG GVGVGYGLVL VGTLRGDVIA
 121 LDEATGKKKW TKRVNSEVLS APATNGDVVV VQTQDDKLIG LDAASGDQRW IYESTVPVLT
 181 LRGTGAPLIA GNMALAGLAS GKVVAVDVQR GLPIWEQRVA IPQGRSELDR VVDIDGGLLL
 241 SGDTLYVVSY QGRAAALDVN SGRLLWQREA SSYVGVAEGF GNIYVSQASG SVEGLDSRGA
 301 SSLWNNDALA RRQLSAPAVF SSNVVVGDLE GYVHLLSQVD GRFVGRERVD SDGVRVRPLV
 361 VGSWMYVFGN GGKLVAYTIR*
```

Figure 7 (SEQ ID NO: 19)
```
   1 ATGCGCAGCC TTCTTCTCTC CGCGCTGGCC CTGCTACCCG CCCTGGCCCT GGCGCAACCC
  61 GACGCCTCGA GCTTCCCTTC CTGCCTCGCC GGCCTGCAGA AGAAGGCCCA GGCGCAGGGC
 121 ATTTCCGCCG ACAGTTATGA GCGCTTCACC AGCGGCCTGC AGGCCGACCT CAGCGTGCTC
 181 GACCTGCTCG ACGCGCAGCC GGAGTTCACC ACCCCGCTGT GGGACTACCT GGCCGGCCTG
 241 GTGGACGAGC AGCGGGTCAG CGATGGCAAG GCGATGCTCG CCCAGCACGA CAAGCTGCTC
 301 GACCAGGTGG CCGCGCGCTA CGGCGTGGAC AAGTACACGG TGGTGGCGGT GTGGGGCGTG
 361 GAAAGCGACT ACGGGCGGAT CTTCGGCAAG CGTCCGCTGC TGACCTCGCT GTCGACCCTG
 421 TCCTGCTACG GCGCCGCCA GTCGTTCTTC CAGGGCGAGT TCCTCGCCAC CCTGAAGCTG
 481 TTGCAGGCCG GCGACATCCG CGACGCCGGC ATCACCGGCT CCTGGGCCGG GGCCTTCGGC
 541 CATACCCAGT TCATGCCATC GACCTACGCG CGGATCGCCG TGGACTTCGA CGGCGACGGT
 601 CGCCGCGACC TGGTAGGCAG CGTGCCGGAT GCCCTCGGTT CCACCGCCAA CTACCTGAAG
 661 AAGGCTGGCT GGCGCACGGG ACAGCCGTGG GGCTATGAAG TGAAGGTGCC GGCCGACTTC
 721 CCCGCCAGCC TGGCCGGGCG CGGCAAGCGC CAGCCGCTGT CGGCCTGGGT CGCCCGTGGG
 781 GTGAGGCGGG TCGACGGCCA GCCGCTGCCG GGCGGCGACG AGAAGGCCGC GATCCTCCTG
 841 CCGGCCGGGG CCCAGGGCCC GGCCTTCCTG GTCTATCGCA ACTACGATGC GATCTATTCC
 901 TACAACGCCG CGGAAAGCTA CGCGCTGGCC ATCGCCCTGC TTTCCGACCG CCTGCGCGGC
 961 GGCAGCGGCC TGGTGGCGTC CTGGCCGACC GACGACCCGG GCATCAGCCG GCTCGAGCGC
1021 AAGCAATTGC AGAAGGCGTT GCTGGCGCGC GGCTACGACA TCGGCGAGGC CGACGGGCTG
1081 ATCGGCACCA GCACGCGCAA GGCGATCCAG GCCGAGCAGA AGCGCCTCGG CCTGACCCCG
1141 GCCGACGGTC GCGCCGGGCG CAAGATCCTC GAGGCGCTGA AGGGCGCCCA GCCCTGA
```

Figure 8 (SEQ ID NO: 20)
```
   1 MRSLLLSSLA LLPALALAQP DASSFPSCLA GLQKKAQAQG ISADSYERFT SGLQADLSVL
  61 DLLDAQPEFT TPLWDYLAGL VDEQRVSDGK AMLAQHDKLL DQVAARYGVD KYTVVAVWGV
 121 ESDYGRIFGK RPLLTSLSTL SCYGRRQSFF QGEFLATLKL LQAGDIRDAG ITGSWAGAFG
 181 HTQFMPSTYA RIAVDFDGDG RRDLVGSVPD ALGSTANYLK KAGWRTGQPW GYEVKVPADF
 241 PASLAGRGKR QPLSAWVARG VRRVDGQPLP GGDEKAAILL PAGAQGPAFL VYRNYDAIYS
 301 YNAAESYALA IALLSDRLRG GSGLVASWPT DDPGISRLER KQLQKALLAR GYDIGEADGL
 361 IGTSTRKAIQ AEQKRLGLTP ADGRAGRKIL EALKGAQP*
```

Figure 9 ( SEQ ID NO: 21)
```
   1 GTGAAGAACG CAATGCAAGT ACTGCGTACA TGGGCGGCCA GGGGCGTCCA ATGGGTCGGC
  61 GTAGCCGGCG TCATTGGCCT GTCCGGGGCG GCCCAGGCGG GGGACTACGA CGGCTCGCCG
 121 CAAGTGGCCG AGTTCGTCAG CGAAATGACC CGCGACTACG GCTTCGCCGG AGAGCAGCTG
 181 ATGGGGCTGT TCCGCGACGT GAACCGCAAG CAGTCGATCC TCGATGCGAT CTCGCGCCCG
 241 GCCGAGCGGG TCAAGCAGTG GAAGGAATAC CGGCCGATCT TCATCAGCGA CGCGCGCATC
 301 AGTCGTGGCG TCGACTTCTG GAACAAGCAT GCCGAAGACC TGGCGCGGGC GGAGAAGGAA
 361 TACGGCGTGC CGGCCGAGAT CATCGTCTCG ATCATCGGCG TGGAAACCTT CTTCGGCCGC
 421 AACACCGGCA GTTACCGGGT GATGGACGCG CTGTCCACCC TCGGCTTCGA CTACCCGCCG
 481 CGGGCCGACT TCTTCCGCAA GGAGTTGCGC GAGTTCCTCC TGCTCGCCCG CAACAGCAG
 541 GTCGACCCGC TCAGCCTGAC CGGCTCCTAC GCCGGCGCCA TGGGCCTGCC ACAATTCATG
 601 CCGAGCAGCT TCCGCGCCTA CGCGGTGGAC TTCGACGGCG ATGGCCACAT CAATATCTGG
 661 AGCGACCCGA CCGATGCCAT CGGTAGCGTC GCCAGCTACT TCAAGCAGCA CGGCTGGGTC
 721 ACCGGCGAGC CGTGGTCTC GGTGGCCGAG ATCAACGACG AGAGCGCCGA GAGCGCGGTG
 781 ACCAGGGGCG TCGACCCGAC CATGAGCCTG GGCGAGCTGC GTGCCCGCGG CTGGCGCACC
 841 CACGATGCGC TGCGCGACGA CCAGAAGGTC ACGGCGATGC GTTTCGTCGG CGACAAGGGC
 901 ATCGAGTATT GGGTCGGTTT GCCGAACTTC TACGTGATCA CCCGCTATAA TCGCAGCGCC
 961 ATGTATGCCA TGGCGGTTTA TCAGCTGGCG GGCGAGATTG CCCGCGCGCG AGGTGCCCAT
1021 TGA
```

Figure 10 (SEQ ID NO: 22)
```
  1 MKNAMQVLRT WAARGVQWVG VAGVIGLSGA AQAGDYDGSP QVAEFVSEMT RDYGFAGEQL
 61 MGLFRDVNRK QSILDAISRP AERVKQWKEY RPIFISDARI SRGVDFWNKH AEDLARAEKE
121 YGVPAEIIVS IIGVETFFGR NTGSYRVMDA LSTLGFDYPP RADFFRKELR EFLLLAREQQ
181 VDPLSLTGSY AGAMGLPQFM PSSFRAYAVD FDGDGHINIW SDPTDAIGSV ASYFKQHGWV
241 TGEPVVSVAE INDESAESAV TRGVDPTMSL GELRARGWRT HDALRDDQKV TAMRFVGDKG
301 IEYWVGLPNF YVITRYNRSA MYAMAVYQLA GEIARARGAH *
```

Figure 11 (SEQ ID NO: 23)
```
   1 ATGCGCCGTA CCGCCCTCGC CCTGCCCCTG TTCCTTCTGG TCTCAGCATG CAGCAGCGAA
  61 CCGACGCCAC CACCGAAACC CGCCGCCAAA CCCCAGGCCC GCACCGTCAT TTCACCCCGC
 121 CCCGTACGCC AGTCGGTGCA ACCGATACTG CCGCTGCGCG GCGATTACGC GAACAATCCG
 181 GCGGCACAGC ACTTCATCGA CAGGATGGTC AGCCAGCACG GCTTCAACCG CCAGCAACTG
 241 CACGATCTGT TCGCCCAGAC CCAGCGCCTG GACTGGGTGA TCCGCCTGAT GGACCGGCAA
 301 GCCCCGACCT ATACCCCACC CAGCGGACCG AACGGCGCCT GGCTGCGCTA CCGGAAGAAG
 361 TTCGTCACGC CAGGCAACGT ACAGAACGGC GTGCTGTTCT GGGACCAATA CGAAACCGAC
 421 CTGCAACGGG CATCGCGCGT CTACGGCGTG CCGCCGGAGA TCATCGTCGG CATCATCGGC
 481 GTGGAAACCC GCTGGGGGCG TGTGATGGGC AAGACGCGGA TCATCGATGC GCTGTCCACC
 541 CTGTCCTTCT CCTACCCTCG CCGCGCGGAA TTCTTCAGCG GCGAACTGGA GCAATTCCTC
 601 CTCCAGGCGC GCAAGGAAGG CACCGACCCG CTGGCCCTGC GCGGTTCCTA TGCCGGCGCC
 661 ATGGGCTACG GCCAGTTCAT GCCGTCTTCA TTCACCAAGT ACGCGGTGGA CTTCGATGGC
 721 GATGGGCATA TCGACCTGTG GAATCCGCGT GACGCCATCG GCAGCGTCGC CAACTATTTC
 781 AGGCAGCACG GCTGGGTCAG CGGCGATCGC GTGGCGGTTC CCGCCAGTGG CCGGGCTCCC
 841 TCGCTGGAAG ATGGCTTCAA GACGCTGTAC CCGCTGGACG TGCTCGCTTC CGCCGGATTA
 901 CGCCCGCAGG GTCCGCTCGG CGGCCACCGG CAAGCCAGCC TGCTGCGCCT GGACATGGGC
 961 AGGAACTACC AGTACTGGTA CGGCCTGCCG AACTTCTACG TGATCACCCG CTATAACCAC
1021 AGCACCCACT ACGCGATGGC CGTCTGGGAA CTGGGCAAGG AAGTCGACCG GGTGCGTCAC
1081 CGCTCCGTCG TCAGGCAGGA TTAG
```

Figure 12 ( SEQ ID NO: 24)
```
  1 MRRTALALPL FLLVSACSSE PTPPPKPAAK PQARTVISPR PVRQSVQPIL PLRGDYANNP
 61 AAQHFIDRMV SQHGFNRQQL HDLFAQTQRL DWVIRLMDRQ APTYTPPSGP NGAWLRYRKK
121 FVTPGNVQNG VLFWDQYETD LQRASRVYGV PPEIIVGIIG VETRWGRVMG KTRIIDALST
181 LSFSYPRRAE FFSGELEQFL LQARKEGTDP LALRGSYAGA MGYGQFMPSS FTKYAVDFDG
241 DGHIDLWNPR DAIGSVANYF KQHGWVSGDR VAVPASGRAP SLEDGFKTLY PLDVLASAGL
301 RPQGPLGGHR QASLLRLDMG RNYQYWYGLP NFYVITRYNH STHYAMAVWE LGKEVDRVRH
361 RSVVRQD*
```

Figure 13

```
              30         40         50         60         70         80
SPA-1     ACAQKNPTVEYNQPAAPLQTKAPFSGAGPAASVPAGAPNEAQP-GQSFEQWRDAFRQQAL
                        |  :||  |    |||  ::||  :       :::::|
SHB-PA104            MRSLLLSSLALLPALA--LAQPDASSFPSCLAGLQKKAQ
                                    10          20         30

90        100        110        120        130        140
SPA-1     AGGIDAQTFDRAFAGVQPDPAVVEADRSQPEFTRPVWKYLEGALDPLRVRQGQARLAQHA
          | ||:|::::|   :|:|  | :|::     :|||||  |:|  || |  :|  || :|:|  ||||
SHB-PA104 AQGISADSYERFTSGLQADLSVLDLLDAQPEFTTPLWDYLAGLVDEQRVSDGKAMLAQHD
             40         50         60         70         80         90

150        160        170        180        190        200
SPA-1     RILGEVDARYAVDADAVVAIWGMESNYGSHMGNKNVIRSLATLAYEGRRPEFAHAQLLAA
          ::|  :|  |||:||   :|||:||:||:||   :|::  ::  ||:||:   |||   |  :::::||:
SHB-PA104 KLLDQVAARYGVDKYTVVAVWGVESDYGRIFGKRPLLTSLSTLSCYGRRQSFFQGEFLAT
            100        110        120        130        140        150

210        220        230        240        250        260
SPA-1     LKILQHGDVPASFMIGSWAGAMGQTQFIPTTHNQYAVDFDGDGKRDIWGSPGDALASTAN
          ||:||  ||:     :   : |||||||:|:|||:|:|: :  ||||||||||:||  ||   |||:||||
SHB-PA104 LKLLQAGDIRDAGITGSWAGAFGHTQFMPSTYARIAVDFDGDGRRDLVGSVPDALGSTAN
            160        170        180        190        200        210

270        280        290        300        310        320
SPA-1     YLKASGWIAGQPWGFEVRLPAGFDYSLAELTIRKPLGEWQGMGVQGVNGGPLPSGLSGEQ
          |||   :||  :|||||:||::||  |    |||        |:||:  '  :  ||:  |:|  |||:|      |:
SHB-PA104 YLKKAGWRTGQPWGYEVKVPADFPASLAGRGKRQPLSAWVARGVRRVDGQPLPGG--DEK
            220        230        240        250        260        270

330        340        350        360        370        380
SPA-1     ASLLLPAGHRGPAFLVLHNFRAILKYNNSSAYALAVGLLADSFKGGGRIVGAWPLEDVPL
          |::||||| :||||||  :|:  ||  :||  :  :||||::||:|  ::||:  :|::||  :|    :
SHB-PA104 AAILLPAGAQGPAFLVYRNYDAIYSYNAAESYALAIALLSDRLGGSGLVASWPTDDPGI
            280        290        300        310        320        330

390        400        410        420        430        440
SPA-1     SRSQRIELQRQLAARGHDPGAVDGIIGANTRKAIRACQQEFGW-PADGYPTPALLDRLRT
          ||  :|  :||:  |   |||:|  |   :||:||::|||||:|  |:::|    ||||        :|:  |:
SHB-PA104 SRLERKQLQKALLARGYDIGEADGLIGTSTRKAIQAEQKRLGLTPADGRAGRKILEALKG
            340        350        360        370        380        390

SPA-1     P

SHB-PA104 AQP
```

Figure 14

```
              70         80         90        100        110
SPA-1     VPAGAPNEAQPGQSFEQWRDAFRQQALAGGIDAQTFDRAFAGVQPDPAVVEADRSQP---
                     ::  :|  |  :|||  |           :::|:|
SHB-PA105 VQWVGVAGVIGLSGAAQAGDYDGSPQVAEFVSEMTRDYGFAGEQLMGLFRDVNRKQSILD
              20         30         40         50         60         70

120        130        140        150        160        170
SPA-1     EFTRPV-----WK-YLEGALDPLRVRQGQARLAQHARILGEVDARYAVDADAVVAIWGME
          ::||:      || |      ::   |: :|      :||: |::::  :|:|  |: :|:|  |:|
SHB-PA105 AISRPAERVKQWKEYRPIFISDARISRGVDFWNKHAEDLARAEKEYGVPAEIIVSIIGVE
               80         90        100        110        120        130

180        190        200        210        220        230
SPA-1     SNYGSHMGNKNVIRSLATLAYE-GRRPEFAHAQLLAALKILQHGDVPASFMIGSWAGAMG
          : :| : |:   |: :|:||:::    | :| : :|      |  :: :|   : :  ||:|||||
SHB-PA105 TFFGRNTGSYRVMDALSTLGFDYPPRADFFRKELREFLLLAREQQVDPLSLTGSYAGAMG
                 140        150        160        170        180        190

240        250        260        270        280        290
SPA-1     QTQFIPTTHNQYAVDFDGDGKRDIWGSPGDALASTANYLKASGWIAGQPWGFEVRLPAGF
          ||:|::  ||||||||||: :||::| ||::|:|:|:|  ||::|:|      |  :
SHB-PA105 LPQFMPSSFRAYAVDFDGDGHINIWSDPTDAIGSVASYFKQHGWVTGEPV---VSVAEIN
                 200        210        220        230        240        250

300        310        320        330        340
SPA-1     DYSLAELTIRKPLGEWQGMGVQGVNGGPLPSGLSGEQ-ASLLLPAGHRGPAFLV-LHNFR
          |  |  || ::  : :     :::|      :  |      ::|   :|  :: :    :| :|   :  |  | ||
SHB-PA105 DES-AESAVTRGVDPTMSLGELRARGWRTHDALRDDQKVTAMRFVGDKGIEYWVGLPNFY
                 260        270        280        290        300        310

350        360        370        380        390        400
SPA-1     AILKYNNSSAYALAVGLLADSFKGGGRIVGAWPLEDVPLSRSQRIELQRQLAARGHDPGA
          :|  :|| |:  ||:||   ||
SHB-PA105 VITRYNRSAMYAMAVYQLAGEIARARGAH
                 320        330        340
```

Figure 15

```
              10         20         30         40         50
SPA-1     MRNPERSALLKVSGLLGSTVVAMGLGL-SSACAQKNPTVEYNQPAAPLQTKAPFSGAGPA
              |::|:  | |   |||:::  ||    :|||  |:::   :|
SHB-PA106        MRRTALALPLFLLVSACSSE-PTPP-PKPAAKPQARTVISPRPVR
                 10         20         30         40

60         70         80         90        100        110
SPA-1     ASVPAGAP--NEAQPGQSFEQWRDAFRQQALAGGIDAQTFDRAFAGVQP-DPAVVEADRS
          ||      |  ::    : : :::  |  : :|     |:: | :   || :|  | ::   ||:
SHB-PA106 QSVQPILPLRGDYANNPAAQHFIDRMVSQH---GFNRQQLHDLFAQTQRLDWVIRLMDRQ
                    50         60         70         80         90        100

120        130        140        150        160        170
SPA-1     QPEFTRP-----VW-KYLEGALDPLRVRQGQARLAQHARILGEVDARYAVDADAVVAIWG
          | :|  |       :| :| :  :  |  |::|    |:   |  :::   |:|   : :|:|  |
SHB-PA106 APTYTPPSGPNGAWLRYRKKFVTPGNVQNGVLFWDQYETDLQRASRVYGVPPEIIVGIIG
                    110        120        130        140        150        160

180        190        200        210        220
SPA-1     MESNYGSHMGNKNVIRSLATLAYE-GRRPEFAHAQLLA-ALKILQHGDVPASFMIGSWAG
          :|:  :|   ||:   :|  :|:||::     ||  ||    ::|       |:     ::|    |  ::    ||:||
SHB-PA106 VETRWGRVMGKTRIIDALSTLSFSYPRRAEFFSGELEQFLLQARKEGTDPLALR-GSYAG
                    170        180        190        200        210

230        240        250        260        270        280
SPA-1     AMGQTQFIPTTHNQYAVDFDGDGKRDIWGSPGDALASTANYLKASGWIAGQPWGFEVRLP
          |||   ||:|::   :::||||||||||: |:|   :|   ||::|:|||:|    ||::|:         :|  :|
SHB-PA106 AMGYGQFMPSSFTKYAVDFDGDGHIDLW-NPRDAIGSVANYFKQHGWVSGD----RVAVP
                220        230        240        250        260        270

290        300        310        320        330        340
SPA-1     A-GFDYSLAE-LTIRKPLGEWQGMGVQGVNGGPLPSGLSGEQASLL-LPAGHRGPAFLVL
          | |    || :: :     ||      : |::      |||  :       :|||||  |   |:       :       |
SHB-PA106 ASGRAPSLEDGFKTLYPLDVLASAGLRP--QGPLGGH---RQASLLRLDMGRNYQYWYGL
                280        290        300         310        320

350        360        370        380        390        400
SPA-1     HNFRAILKYNNSSAYALAVGLLADSFKGGGRIVGAWPLEDVPLSRSQRIELQRQLAARGH
          ||  :|  :||:|:   ||:||
SHB-PA106 PNFYVITRYNHSTHYAMAVWELGKEVDRVRHRSVVRQD
                   330        340        350        360
```

POLYPEPTIDES OF *PSEUDOMONAS AERUGINOSA*

CROSS-REFERENCE TO RELATED APPLICATION

This application claims the benefit of U.S. Provisional Application No. 60/331,221 filed on Nov. 13, 2001 and is incorporated by reference herein.

FIELD OF THE INVENTION

The present invention is related to polypeptides, more particularly SPA-1, SPA-2 and SPA-3 polypeptides of *Pseudomonas aeruginosa* which may be used to prevent, diagnose and/or treat *Pseudomonas aeruginosa* infection.

BACKGROUND OF THE INVENTION

*Pseudomonas aeruginosa* is a prevalent opportunistic bacterial pathogen in humans and animals. *P. aeruginosa* is the most common Gram-negative bacterium found in nosocomial infections, especially in immunocompromised individuals. It is frequently related to ventilator-associated pneumonia in intubated patients. *Pseudomonas* infection is common amongst patients with cystic fibrosis, burn wounds, organ transplants, and intravenous-drug addiction. Cystic fibrosis patients are often chronically infected by *P. aeruginosa*, which is responsible for increased illness and death in this particular population. *P. aeruginosa* bacteremia is responsible for high death rates in burn units. *Pseudomonas* can lead to serious conditions such as endophthalmitis, endocarditis, meningitis, pneumonia, and septicaemia. Septicemia due to *P. aeruginosa* is associated with the highest death rates of all Gram-negative infections.

Since *P. aeruginosa* is naturally resistant to many antibiotics, there is a need for the development of a vaccine that will protect individuals from *P. aeruginosa* infection. An infection by *P. aeruginosa* induces an immune response against antigens found at the surface of the bacterial cells. However, many of these surface proteins are still not characterized, nor has the immune response resulting in protection from infection by different strains been determined.

To develop a vaccine that will protect individuals from. *P. aeruginosa* infection, efforts have mainly been concentrated on lipopolysaccharides (LPS). However, even though a limited number of LPS serotypes are associated with clinical cases, the production of a multivalent LPS-based vaccine is complex and may induce serotype replacement in vaccinated individuals. Anti-flagellar and anti-pili vaccines are also evaluated but the regulation of flagella/pili expression at different *P. aeruginosa* infection stages may prevent effective protection. Outer membrane proteins (OMP) are also being tested. An OMP preparation from 4 different *P. aeruginosa* serotypes is currently in clinical trials but the specificity of the protection confered by this preparation remains to be evaluated. A recombinant fusion protein, based on outer membrane proteins OprF and OprI, is considered a promising vaccine candidate. However, the OprF protein was shown to be absent from some clinical strains of *P. aeruginosa* and the protection confered by the OprI protein alone has not been evaluated yet.

A review of existing technology is described in Stanislavsky E S and Lam J S. (1997) FEMS Microbiol. Rev. 21(3): 243-77 and Holder I A. (2001) J. Burn Care Rehabil. 22(5): 311-20.

The sequence of the genome of *P. aeruginosa* strain PAO1 was determined in a collaboration among the Cystic Fibrosis Foundation, the University of Washington and Pathogenesis Corporation and is available at the Internet site (http://www): *pseudomonas*.com/, the Internet site (http://www): tigr.org/tigr-scripts/CMR2/Genome Page3.spl?database=n tpa03, the Internet site (http://) *pseudomonas*.bit.uq.edu.au/ and in *Nature*, Stover et al. 406:959-964 (2000).

Therefore there remains an unmet need for *P. aeruginosa* polypeptides that may be used to prevent, diagnose and/or treat *P. aeruginosa* infection.

SUMMARY OF THE INVENTION

According to one aspect, the present invention provides an isolated polynucleotide encoding a polypeptide having at least 70% identity to a second polypeptide comprising a sequence chosen from SEQ ID Nos: 2, 4, 6, 8, 10, 12 or fragments or analogs thereof.

According to one aspect, the present invention relates to polypeptides comprising a sequence chosen from SEQ ID No: 2, 4, 6, 8, 10, 12 or fragments or analogs thereof.

In other aspects, there are provided polypeptides encoded by polynucleotides of the invention, pharmaceutical compositions, vectors comprising polynucleotides of the invention operably linked to an expression control region, as well as host cells transfected with said vectors and processes for producing polypeptides comprising culturing said host cells under conditions suitable for expression.

BRIEF DESCRIPTION OF THE DRAWINGS

FIG. 1 represents the DNA sequence of SPA-1 gene from *P. aeruginosa* strain PAO1; SEQ ID NO: 1. The underlined portion of the sequence represents the leader peptide coding region.

FIG. 2 represents the amino acid sequence of SPA-1 polypeptide from *P. aeruginosa* strain PAO1; SEQ ID NO: 2. The underlined sequence represents the 32 amino acid residues leader peptide.

FIG. 3 represents the DNA sequence of SPA-2 gene from *P. aeruginosa* strain PAO1; SEQ ID NO: 3. The underlined portion of the sequence represents the leader peptide coding region.

FIG. 4 represents the amino acid sequence of SPA-2 polypeptide from *P. aeruginosa* strain PAO1; SEQ ID NO: 4. The underlined sequence represents the 19 amino acid residues leader peptide.

FIG. 5 represents the DNA sequence of SPA-3 gene from *P. aeruginosa* strain PAO1; SEQ ID NO: 5. The underlined portion of the sequence represents the leader peptide coding region.

FIG. 6 represents the amino acid sequence of SPA-3 polypeptide from *P. aeruginosa* strain PAO1; SEQ ID NO: 6. The underlined sequence represents the 21 amino acid residues leader peptide.

FIG. 7 represents the DNA sequence of SHB-PA104 gene from *P. aeruginosa* strain PAO1; SEQ ID NO: 19. The underlined portion of the sequence represents the leader peptide-coding region.

FIG. 8 represents the amino acid sequence of SHB-PA104 protein from *P. aeruginosa* strain PAO1; SEQ ID NO: 20. The underlined sequence represents the 16 amino acid residues leader peptide.

FIG. 9 represents the DNA sequence of. SHB-PA105 gene from *P. aeruginosa* strain PAO1; SEQ ID NO: 21. The underlined portion of, the sequence represents the leader peptide-coding region.

FIG. 10 represents the amino acid sequence of SHB-PA105 protein from *P. aeruginosa* strain PAO1; SEQ ID NO: 22. The underlined sequence represents the 33 amino acid residues leader peptide.

FIG. 11 represents the DNA sequence of SHB-PA106 gene from *P. aeruginosa* strain PAO1; SEQ ID NO: 23. The underlined portion of the sequence represents the leader peptide-coding region.

FIG. 12 represents the amino acid sequence of SHB-PA106 protein from *P. aeruginosa* strain PAO1; SEQ ID NO: 24. The underlined sequence represents the 16 amino acid residues leader peptide.

FIG. 13 represents the protein sequence alignment of SPA-1 protein (SEQ ID NO:31) with SHB-PA104 (without leader peptides) (SEQ ID NO:32) from PAO1 strain. |, identical amino acids; :, conserved amino acids.

FIG. 14 represents the protein sequence alignment of SPA-1 protein (SEQ ID NO:33) with SHB-PA105 (without leader peptides) (SEQ ID NO:34) from PAO1 strain. |, identical amino acids; :, conserved amino acids.

FIG. 15 represents the protein sequence alignment of SPA-1. protein (SEQ ID NO:35) with SHB-PA106 (without leader peptides) (SEQ ID NO:36) from PAO1 strain. |, identical amino acids; :, conserved amino acids.

DETAILED DESCRIPTION OF THE INVENTION

The present invention provides purified and isolated polynucleotides, which encode *Pseudomonas* polypeptides which may be used to prevent, diagnose and/or treat *Pseudomonas* infection.

According to one aspect, the present invention provides an isolated polynucleotide encoding a polypeptide having at least 70% identity to a second polypeptide comprising a sequence chosen from SEQ ID NOS: 2, 4, 6, 8, 10, 12 or fragments or analogs thereof.

According to one aspect, the present invention provides an isolated polynucleotide encoding a polypeptide having at least 80% identity to a second polypeptide comprising a sequence chosen from SEQ ID NOS: 2, 4, 6, 8, 10, 12 or fragments or analogs thereof.

According to one aspect, the present invention provides an isolated polynucleotide encoding a polypeptide having at least 90% identity to a second polypeptide comprising a sequence chosen from SEQ ID NOS: 2, 4, 6, 8, 10, 12 or fragments or analogs thereof.

According to one aspect, the present invention provides an isolated polynucleotide encoding a polypeptide having at least 95% identity to a second polypeptide comprising a sequence chosen from SEQ ID NOS: 2, 4, 6, 8, 10, 12 or fragments or analogs thereof.

According to one aspect, the present invention provides an isolated polynucleotide encoding a polypeptide having at least 98% identity to a second polypeptide comprising a sequence chosen from SEQ ID NOS: 2, 4, 6, 8, 10, 12 or fragments or analogs thereof.

According to one aspect, the present invention provides an isolated polynucleotide encoding a polypeptide having at least 70% identity to a second polypeptide comprising SEQ ID NOS: 2, 4, 6, 8, 10 or 12.

According to one aspect, the present invention provides an isolated polynucleotide encoding a polypeptide having at least 80% identity to a second polypeptide comprising SEQ ID NOS: 2, 4, 6, 8, 10 or 12.

According to one aspect, the present invention provides an isolated polynucleotide encoding a polypeptide having at least 90% identity to a second polypeptide comprising SEQ ID NOS: 2, 4, 6, 8, 10 or 12.

According to one aspect, the present invention provides an isolated polynucleotide encoding a polypeptide having at least 95% identity to a second polypeptide comprising SEQ ID NOS: 2, 4, 6, 8, 10 or 12.

According to one aspect, the present invention provides an isolated polynucleotide encoding a polypeptide having at least 98% identity to a second polypeptide comprising SEQ ID NOS: 2, 4, 6, 8, 10 or 12.

According to one aspect, the present invention relates to polypeptides which comprise an amino acid sequence selected from SEQ ID Nos: 2, 4, 6, 8, 10, 12 or fragments or analogs thereof.

According to one aspect, the present invention relates to polypeptides which comprise an amino acid sequence selected from SEQ ID Nos: 2, 4, 6, 8, 10 or 12.

According to one aspect, the present invention relates to polypeptides characterized by the amino acid sequence comprising SEQ ID NOS: 2, 4, 6, 8, 10; 12 or fragments or analogs thereof.

According to one aspect, the present invention relates to polypeptides characterized by the amino acid sequence comprising SEQ ID NOS: 2, 4, 6, 8, 10 or 12.

According to one aspect, the present invention provides a polynucleotide encoding an epitope bearing portion of a polypeptide comprising a sequence chosen from SEQ ID NOS: 2, 4, 6, 8, 10, 12 or fragments or analogs thereof.

According to one aspect, the present invention provides a polynucleotide encoding an epitope bearing portion of a polypeptide comprising a sequence chosen from SEQ ID NOS: 2, 4, 6, 8, 10 or 12.

According to one aspect, the present invention relates to epitope bearing portions of a polypeptide comprising a sequence chosen from SEQ ID NOS: 2, 4, 6, 8, 10, 12 or fragments or analogs thereof.

According to one aspect, the present invention relates to epitope bearing portions of a polypeptide comprising a sequence chosen from SEQ ID NOS: 2, 4, 6, 8, 10 or 12.

According to one aspect, the present invention provides an isolated polynucleotide comprising a polynucleotide chosen from:

(a) a polynucleotide encoding a polypeptide having at least 70% identity to a second polypeptide comprising a sequence chosen from: SEQ ID NOS: 2, 4, 6, 8, 10, 12 or fragments or analogs thereof;

(b) a polynucleotide encoding a polypeptide having at least 80% identity to a second polypeptide comprising a sequence chosen from: SEQ ID NOS: 2, 4, 6, 8, 10, 12 or fragments or analogs thereof;

(c) a polynucleotide encoding a polypeptide having at least 95% identity to a second polypeptide comprising a sequence chosen from: SEQ ID NOS: 2, 4, 6, 8, 10, 12 or fragments or analogs thereof;

(d) a polynucleotide encoding a polypeptide comprising a sequence chosen from: SEQ ID NOS: 2, 4, 6, 8, 10, 12 or fragments or analogs thereof;

(e) a polynucleotide encoding a polypeptide capable of raising antibodies having binding specificity for a polypeptide comprising a sequence chosen from: SEQ ID NOS: 2, 4, 6, 8, 10, 12 or fragments or analogs thereof;

(f) a polynucleotide encoding an epitope bearing portion of a polypeptide comprising a sequence chosen from SEQ ID NOS: 2, 4, 6, 8, 10, 12 or fragments or analogs thereof;

(g) a polynucleotide comprising a sequence chosen from SEQ ID NOS: 1, 3, 5, 7, 9, 11 or fragments or analogs thereof;
(h) a polynucleotide that is complementary to a polynucleotide in (a), (b), (c), (d), (e), (f) or (g).

According to one aspect, the present invention provides an isolated polynucleotide comprising a polynucleotide chosen from:
(a) a polynucleotide encoding a polypeptide having at least 70% identity to a second polypeptide comprising a sequence chosen from: SEQ ID NOS: 2, 4, 6, 8, 10 or 12;
(b) a polynucleotide encoding a polypeptide having at least 80% identity to a second polypeptide comprising a sequence chosen from: SEQ ID NOS: 2, 4, 6, 8, 10 or 12;
(c) a polynucleotide encoding a polypeptide having at least 95% identity to a second polypeptide comprising a sequence chosen from: SEQ ID NOS: 2, 4, 6, 8, 10 or 12;
(d) a polynucleotide encoding a polypeptide comprising a sequence chosen from: SEQ ID NOS: 2, 4, 6, 8, 10 or 12;
(e) a polynucleotide encoding a polypeptide capable of raising antibodies having binding specificity for a polypeptide comprising a sequence chosen from: SEQ ID NOS: 2, 4, 6, 8, 10 or 12;
(f) a polynucleotide encoding an epitope bearing portion of a polypeptide comprising a sequence chosen from SEQ ID NOS: 2, 4, 6, 8, 10 or 12;
(g) a polynucleotide comprising a sequence chosen from SEQ ID NOS: 1, 3, 5, 7, 9 or 11;
(h) a polynucleotide that is complementary to a polynucleotide in (a), (b), (c), (d), (e), (f) or (g).

According to one aspect, the present invention provides an isolated polypeptide comprising a polypeptide chosen from:
(a) a polypeptide having at least 70% identity to a second polypeptide comprising a sequence chosen from SEQ ID NOS: 2, 4, 6, 8, 10 or 12 or fragments or analogs thereof;
b) a polypeptide having at least 80% identity to a second polypeptide comprising a sequence chosen from SEQ ID NOS: 2, 4, 6, 8, 10 or 12 or fragments or analogs thereof;
c) a polypeptide having at least 95% identity to a second polypeptide comprising a sequence chosen from SEQ ID NOS: 2, 4, 6, 8, 10 or 12 or fragments or analogs thereof;
d) a polypeptide comprising a sequence chosen from SEQ ID NOS: 2, 4, 6, 8, 10 or 12 or fragments or analogs thereof;
(e) a polypeptide capable of raising antibodies having binding specificity for a polypeptide comprising a sequence chosen from SEQ ID NOS: 2, 4, 6, 8, 10 or 12 or fragments or analogs thereof;
(f) an epitope bearing portion of a polypeptide comprising a sequence chosen from SEQ ID NOS: 2, 4, 6, 8, 10 or 12 or fragments or analogs thereof;
(g) the polypeptide of (a), (b), (c), (d), (e) or (f) wherein the N-terminal Met residue is deleted;
(h) the polypeptide of (a), (b), (c), (d), (e), (f) or (g) wherein the secretory amino acid sequence is deleted.

According to one aspect, the present invention provides an isolated polypeptide comprising a polypeptide chosen from:
(a) a polypeptide having at least 70% identity to a second polypeptide comprising a sequence chosen from SEQ ID NOS: 2, 4, 6, 8, 10 or 12;
(b) a polypeptide having at least 80% identity to a second polypeptide comprising a sequence chosen from SEQ ID NOS: 2, 4, 6, 8, 10 or 12;
(c) a polypeptide having at least 95% identity to a second polypeptide comprising a sequence chosen from SEQ ID NOS: 2, 4, 6, 8, 10 or 12;
(d) a polypeptide comprising a sequence chosen from SEQ ID NOS: 2, 4, 6, 8, 10 or 12;
(e) a polypeptide capable of raising antibodies having binding specificity for a polypeptide comprising a sequence chosen from SEQ ID NOS: 2, 4, 6, 8, 10 or 12;
(f) an epitope bearing portion of a polypeptide comprising a sequence chosen from SEQ ID NOS: 2, 4, 6, 8, 10 or 12;
(g) the polypeptide of (a), (b), (c), (d), (e) or (f) wherein the N-terminal Met residue is deleted;
(h) the polypeptide of (a), (b), (c), (d), (e), (f) or (g) wherein the secretory amino acid sequence is deleted.

Those skilled in the art will appreciate that the invention includes DNA molecules, i.e. polynucleotides, their homologous sequences and their complementary sequences that encode analogs such as mutants, variants, homologs and derivatives of such polypeptides, as described herein in the present patent application. Homologous genes are evolutionary related, have similar sequences and are structurally related. The invention also includes RNA molecules corresponding to the DNA molecules of the invention. In addition to the DNA and RNA molecules, the invention includes the corresponding polypeptides and monospecific antibodies that specifically bind to such polypeptides.

In a further embodiment, the polypeptides in accordance with the present invention are antigenic.

In a further embodiment, the polypeptides in accordance with the present invention are immunogenic.

In a further embodiment, the polypeptides in accordance with the present invention can elicit an immune response in a host.

In a further embodiment, the present invention also relates to polypeptides which are able to raise antibodies having binding specificity to the polypeptides of the present invention as defined above.

An antibody that "has binding specificity" is an antibody that recognizes and binds the selected polypeptide but which does not substantially recognize and bind other molecules in a sample, e.g., a biological sample. Specific binding can be measured using an ELISA assay in which the selected polypeptide is used as an antigen.

In accordance with the present invention, "protection" in the biological studies is defined by a significant increase in the survival curve, rate or period. Statistical analysis using the Log rank test to compare survival curves, and Fisher exact test to compare survival rates and numbers of days to death, respectively, might be useful to calculate P values and determine whether the difference between the two groups is statistically significant. P values of 0.05 are regarded as not significant.

In an additional aspect of the invention there are provided antigenic/immunogenic fragments of the polypeptides of the invention, or of analogs thereof.

The fragments of the present invention should include one or more such epitopic regions or be sufficiently similar to such regions to retain their antigenic/immunogenic properties. Thus, for fragments according to the present invention the degree of identity is perhaps irrelevant, since they may be 100% identical to a particular part of a polypeptide or analog thereof as described herein. The present invention further provides fragments having at least 10 contiguous amino acid residues from the polypeptide sequences of the present invention. In one embodiment, at least 15 contiguous amino acid residues. In one embodiment, at least 20 contiguous amino acid residues.

The skilled person will appreciate that analogs of the polypeptides of the invention will also find use in the context of the present invention, i.e. as antigenic/immunogenic material. Thus, for instance proteins or polypeptides which include one or more additions, deletions, substitutions or the like are encompassed by the present invention.

As used herein, "fragments", "analogs" or "derivatives" of the polypeptides of the invention include those polypeptides in which one or more of the amino acid residues are substituted with a conserved or non-conserved amino acid residue (preferably conserved) and which may be natural or unnatural. In one embodiment, derivatives and analogs of polypeptides of the invention will have about 70% identity with those sequences illustrated in the figures or fragments thereof. That is, 70% of the residues are the same. In a further embodiment, polypeptides will have greater than 80% identity. In a further embodiment, polypeptides will have greater than 85% identity. In a further embodiment, polypeptides will have greater than 90% identity. In a further embodiment, polypeptides will have greater than 95% identity. In a further embodiment, polypeptides will have greater than 99% identity. In a further embodiment, analogs of polypeptides of the invention will have fewer than about 20 amino acid residue substitutions, modifications or deletions and more preferably less than 10.

In a further embodiment, polypeptides will have greater than 70% homology. In a further embodiment, polypeptides will have greater than 75% homology. In a further embodiment, polypeptides will have greater than 80% homology. In a further embodiment, polypeptides will have greater than 85% homology. In a further embodiment, polypeptides will have greater than 90% homology. In a further embodiment, polypeptides will have greater than 95% homology. In a further embodiment, polypeptides will have greater than 99% homology. In a further embodiment, derivatives and analogs of polypeptides of the invention will have less than about 20 amino acid residue substitutions, modifications or deletions and more preferably less than 10. Preferred substitutions are those known in the art as conserved i.e. the substituted residues share physical or chemical properties such as hydrophobicity, size, charge or functional groups.

These substitutions are those having a minimal influence on the secondary structure and hydropathic nature of the polypeptide. Preferred substitutions are those known in the art as conserved, i.e. the substituted residues share physical or chemical properties such as hydrophobicity, size, charge or functional groups. These include substitutions such as those described by Dayhoff, M. in Atlas of Protein Sequence and Structure 5, 1978 and by Argos, P. in EMBO J. 8, 779-785, 1989. For example, amino acids, either natural or unnatural, belonging to one of the following groups represent conservative changes:

ala, pro, gly, gln, asn, ser, thr, val;
cys, ser, tyr, thr;
val, ile, leu, met, ala, phe;
lys, arg, orn, his;
and phe, tyr, trp, his.

The preferred substitutions also include substitutions of D-enantiomers for the corresponding L-amino acids.

In an alternative approach, the analogs could be fusion polypeptides, incorporating moieties which render purification easier, for example by effectively tagging the desired polypeptide. It may be necessary to remove the "tag" or it may be the case that the fusion polypeptide itself retains sufficient antigenicity to be useful.

The percentage of homology is defined as the sum of the percentage of identity plus the percentage of similarity or conservation of amino acid type.

In one embodiment, analogs of polypeptides of the invention will have about 70% homology with those sequences illustrated in the figures or fragments thereof. In a further embodiment, polypeptides will have greater than 80% homology. In a further embodiment, polypeptides will have greater than 85% homology. In a further embodiment, polypeptides will have greater than 90% homology. In a further embodiment, polypeptides will have greater than 95% homology. In a further embodiment, polypeptides will have greater than 99% homology. In a further embodiment, analogs of polypeptides of the invention will have fewer than about 20 amino acid residue substitutions, modifications or deletions and more preferably less than 10.

One can use a program such as the CLUSTAL program to compare amino acid sequences. This program compares amino acid sequences and finds the optimal alignment by inserting spaces in either sequence as appropriate. It is possible to calculate amino acid identity or homology for an optimal alignment. A program like BLASTx will align the longest stretch of similar sequences and assign a value to the fit. It is thus possible to obtain a comparison where several regions of similarity are found, each having a different score. Both types of identity analysis are contemplated in the present invention.

In an alternative approach, the analogs or derivatives could be fusion polypeptides, incorporating moieties which render purification easier, for example by effectively tagging the desired protein or polypeptide, it may be necessary to remove the "tag" or it may be the case that the fusion polypeptide itself retains sufficient antigenicity to be useful.

It is well known that it is possible to screen an antigenic polypeptide to identify epitopic regions, i.e. those regions which are responsible for the polypeptide's antigenicity or immunogenicity. Methods for carrying out such screening are well known in the art. Thus, the fragments of the present invention should include one or more such epitopic regions or be sufficiently similar to such regions to retain their antigenic/immunogenic properties.

In an additional aspect of the invention there are provided antigenic/immunogenic fragments of the proteins or polypeptides of the invention, or of analogs or derivatives thereof.

Thus, what is important for analogs, derivatives and fragments is that they possess at least a degree of the antigenicity/immunogenicity of the protein or polypeptide from which they are derived.

Also included are polypeptides which have fused thereto other compounds which alter the polypeptides biological or pharmacological properties i.e. polyethylene glycol (PEG) to increase half-life; leader or secretory amino acid sequences for ease of purification; prepro- and pro-sequences; and (poly)saccharides.

Furthermore, in those situations where amino acid regions are found to be polymorphic, it may be desirable to vary one or more particular amino acids to more effectively mimic the different epitopes of the different *Pseudomonas* strains.

Moreover, the polypeptides of the present invention can be modified by terminal —NH, acylation (eg. by acetylation, or thioglycolic acid amidation, terminal carboxy amidation, e.g. with ammonia or methylamine) to provide stability, increased hydrophobicity for linking or binding to a support or other molecule.

Also contemplated are hetero and homo polypeptide multimers of the polypeptide fragments and analogs. These polymeric forms include, for example, one or more polypeptides that have been cross-linked with cross-linkers such as avidin/biotin, gluteraldehyde or dimethylsuperimidate. Such polymeric forms also include polypeptides containing two or more tandem or inverted contiguous sequences, produced from multicistronic mRNAs generated by recombinant DNA technology.

In a further embodiment, the present invention also relates to chimeric polypeptides which comprise one or more polypeptides or fragments or analogs thereof as defined in the figures of the present application.

In a further embodiment, the present invention also relates to chimeric polypeptides comprising two or more polypeptides having a sequence chosen from SEQ ID NOS: 2, 4, 6, 8, 10, 12 or fragments or analogs thereof; provided that the polypeptides are linked as to form a chimeric polypeptide.

In a further embodiment, the present invention also relates to chimeric polypeptides comprising two or more polypeptides comprising a sequence chosen from SEQ ID NOS: 2, 4, 6, 8, 10 or 12 provided that the polypeptides are linked as to form a chimeric polypeptide.

Preferably, a fragment, analog or derivative of a polypeptide of the invention will comprise at least one antigenic region i.e. at least one epitope.

In order to achieve the formation of antigenic polymers (i.e. synthetic multimers), polypeptides may be utilized having bishaloacetyl groups, nitroarylhalides, or the like, where the reagents being specific for thio groups. Therefore, the link between two mercapto groups of the different polypeptides may be a single bond or may be composed of a linking group of at least two, typically at least four, and not more than 16, but usually not more than about 14 carbon atoms.

In a particular embodiment, polypeptide fragments and analogs of the invention do not contain a methionine (Met) starting residue. Preferably, polypeptides will not incorporate a leader or secretory sequence (signal sequence). The signal portion of a polypeptide of the invention may be determined according to established molecular biological techniques. In general, the polypeptide of interest may be isolated from a *Pseudomonas* culture and subsequently sequenced to determine the initial residue of the mature protein and therefore the sequence of the mature polypeptide.

Such an immunogenic fragment may include, for example, the polypeptide of the invention lacking an N-terminal leader peptide, and/or a transmembrane domain and/or external loops and/or turns.

The present invention further provides a fragment of the polypeptide comprising substantially all of the extra cellular domain of a polypeptide which has at least 70% identify, preferably 80% identity, more preferably 95% identity, to a second polypeptide comprising Seq. ID No. 2, 4, 6, 8, 10, 12 or fragments or analogs thereof, over the entire length of said sequence.

It is understood that polypeptides can be produced and/or used without their start codon (methionine or valine) and/or without their leader peptide to favor production and purification of recombinant polypeptides. It is known that cloning genes without sequences encoding leader peptides will restrict the polypeptides to the cytoplasm of *E. coli* and will facilitate their recovery (Glick, B. R. and Pasternak, J. J. (1998) Manipulation of gene expression in prokaryotes. In "Molecular biotechnology: Principles and applications of recombinant DNA", 2nd edition, ASM Press, Washington D.C., p. 109-143).

According to another aspect of the invention, there are also provided (i) a composition of matter containing a polypeptide of the invention, together with a carrier, diluent or adjuvant; (ii) a pharmaceutical composition comprising a polypeptide of the invention and a carrier, diluent or adjuvant; (iii) a vaccine comprising a polypeptide of the invention and a carrier, diluent or adjuvant; (iv) a method for inducing an immune response against *Pseudomonas*, in a host, by administering to the host, an immunogenically effective amount of a polypeptide of the invention to elicit an immune response, e.g., a protective immune response to *Pseudomonas*; and particularly, (v) a method for preventing and/or treating a *Pseudomonas* infection, by administering a prophylactic or therapeutic amount of a polypeptide of the invention to a host in need.

According to another aspect of the invention, there are also provided (i) a composition of matter containing a polynucleotide of the invention, together with a carrier, diluent or adjuvant; (ii) a pharmaceutical composition comprising a polynucleotide of the invention and a pharmaceutically acceptable carrier, diluent or adjuvant; (iii) a method for inducing an immune response against *Pseudomonas*, in a host, by administering to the host, an immunogenically effective amount of a polynucleotide of the invention to elicit an immune response, e.g., a protective immune response to *Pseudomonas*; and particularly, (iv) a method for preventing and/or treating a *Pseudomonas* infection, by administering a prophylactic or therapeutic amount of a polynucleotide of the invention to a host in need.

According to another aspect of the invention, there are also provided (i) a composition of matter containing a polypeptide of the invention, together with a liposome, carrier, diluent or adjuvant; (ii) a pharmaceutical composition comprising a polypeptide of the invention and a liposome, carrier, diluent or adjuvant; (iii) a vaccine comprising a polypeptide of the invention and a liposome, carrier, diluent or adjuvant; (iv) a method for inducing an immune response against *P. aeruginosa*, in a host, by administering to the host, an immunogenically effective amount of a pharmaceutical composition of the invention to elicit an immune response, e.g., a protective immune response to *P. aeruginosa*; and particularly, (v) a method for preventing and/or treating a *P. aeruginosa* infection, by administering a prophylactic or therapeutic amount of a pharmaceutical composition of the invention to a host in need.

According to another aspect of the invention, there are also provided (i) a composition of matter containing a polynucleotide of the invention, together with a liposome, carrier, diluent or adjuvant; (ii) a pharmaceutical composition comprising a polynucleotide of the invention and a liposome, carrier, diluent or adjuvant; (iii) a method for inducing an immune response against *P. aeruginosa*, in a host, by administering to the host, an immunogenically effective amount of a pharmaceutical composition of the invention to elicit an immune response, e.g., a protective immune response to *P. aeruginosa*; and particularly, (iv) a method for preventing and/or treating a *P. aeruginosa* infection, by administering a prophylactic or therapeutic amount of a pharmaceutical composition of the invention to a host in need.

In a further embodiment, the polypeptides of the invention are associated with the liposomes.

As used herein, "associated with" means that the polypeptides of the invention are at least partially embedded in the liposome membrane, and preferably are not covalently linked to the lipids. The polypeptides may also be bonded to a lipid fatty acid "tail" which itself is embedded in the membrane.

In a further embodiment, the pharmaceutical compositions comprising a liposome associated with polypeptides in accordance with the present invention are antigenic.

In a further embodiment, the pharmaceutical compositions comprising a liposome associated with polypeptides in accordance with the present invention are immunogenic.

In a further embodiment, the pharmaceutical compositions comprising a liposome associated with polypeptides in accordance with the present invention can elicit an immune response in a host.

In a further embodiment, the present invention also relates to pharmaceutical compositions comprising a liposome associated with polypeptides which are able to raise antibodies having binding specificity to the polypeptides of the present invention as defined above.

In an additional aspect of the invention there are provided pharmaceutical compositions comprising a liposome associated with immunogenic and/or antigenic fragments of the polypeptides of the invention, or of analogs thereof.

The present invention further provides pharmaceutical compositions comprising a liposome associated with fragments which comprise a B-cell or T-helper epitope.

The present invention further provides pharmaceutical compositions comprising a liposome associated with fragment that may be part of a larger polypeptide. It can be advantageous to include an additional amino acid sequence which contains secretory or leader sequences, or sequences which aid in purification such as multiple histidine residues, or an additional sequence which increases stability during recombinant production, or an additional polypeptide or lipid tail sequences which increase the immunogenic potential of the final polypeptide.

The skilled person will appreciate that pharmaceutical compositions comprising a liposome associated with analogs of the polypeptides of the invention will also find use in the context of the present invention, i.e. as antigenic/immunogenic material. Thus, for instance proteins or polypeptides which include one or more additions, deletions, substitutions or the like are encompassed by the present invention.

In a further embodiment, the present invention also relates to pharmaceutical compositions comprising a liposome associated with chimeric polypeptides which comprise one or more polypeptides or fragments or analogs thereof of the invention.

Liposomes are made of phospholipids and other polar amphiles, which form closed concentric bilayer membranes [summarized in Gregoriades, G., Immunology Today, 11, 3, 89 (1990); Lasic, D., American Scientist, 80, p. 20 (1992); Remington's on Pharmaceutical Sciences, 18th ed., 1990, Mack Publishing Co., Pennsylvania., p. 1691]. The primary constituent of liposomes are lipids, which have a polar hydrophilic "head" attached to a long, nonpolar, hydrophobic "tail". The hydrophilic head typically consists of a phosphate group, while the hydrophobic tail is made of two long hydrocarbon chains. Since the lipid molecules have one part that is water-soluble and another part that is not, they tend to aggregate in ordered structures that sequester the hydrophobic tails from water molecules. In the process, liposomes can entrap water and solutes in their interior, or molecules with hydrophobic regions can also be incorporated directly into the liposomal membranes. Many phospholipids, alone or in combination, with other lipids will form liposomes. By convention, liposomes are categorized by size, and a 3-letter acronym is used to designate the type of liposome being discussed. Multilamellar vesicles are designated "MLV", large unilamellar vesicles "LUV", small unilamellar vesicles "SUV". These designations are sometimes followed by the chemical composition of the liposome. Nomenclature and a summary of known liposomes is described in Storm et al, 1998, PSIT, 1:19-31. Liposomes are efficient in helping membrane proteins refolding and are also efficient adjuvant boosting the humoral as well as the cellular immune response against an antigen.

The invention provides pharmaceutical compositions comprising liposomes constituted from phospholipids. These phospholipids can be synthetized or extracted from bacterial cells, soybean, eggs.

The invention provides a process for the incorporation of polypeptides of the invention into different liposome formulations.

Liposomes can be prepared with various synthetic phospholipids (List 1) or bacterial phospholipids and/or cholesterol, which can be combined at different ratios.

The invention provides a method for extracting lipids from bacterial cells in order to generate liposome formulations from bacterial origin. Complex lipid mixtures can be extracted from several bacterial species. These species could include but are not limited to: *Neisseria* spp, *Haemophilus* spp, *Pseudomonas* spp, *Bacteriodes* spp, *Legionella* spp, *Vibrio* spp, *Brucella* spp, *Bordetella* spp, *Campylobacter* spp, *Klebsiella* spp, *Salmonella* spp, *Shigella* spp, *Proteus* spp, and *Yersinia* spp. Other species can be found in Bergey's Manual of Determinative Bacteriology (1974) (Baltimore).

The liposomes of the invention can be prepared from a variety of vesicle-forming lipids including phosphatidyl ethers and esters, such as phosphatidylethanloamine (PE), phosphatidylserine (PS), phosphatidylglycerol (PG) and phosphatidylcholine (PC) but also from glycerides, such as dioleoylglycerosuccinate; cerebrosides; gangliosides, sphyngomyelin; steroids, such as cholesterol; and other lipids, as well as excipients such as Vitamin E or Vitamin C palmitate.

The fluidity and stability of the liposomal membrane will depend on the transition temperature (temperature at which hydrocarbon regions change from a quasicrystalline to a more fluid state) of the phospholipids.

Modifications of membrane fluidity, number of lamellae, vesicle size, surface charge, lipid to antigen ratio and localization of the antigen within the liposome can modulate the ajduvanticity of liposomal preparations.

The preparation of liposomes can be made by a number of different techniques including ethanol injection; ether infusion; detergent removal; solvent evaporation; evaporation of organic solvents from chloroform in water emulsions; extrusion of multilamellar vesicles through a nucleopore polycarbonate membrane; freezing and thawing of phospholipid mixtures, as well as sonication and homogenization.

Lipids can be dissolved in a suitable organic solvent or mixture of organic solvents, such as a chloroform:methanol solution in a round bottom glass flask and dried using a rotatory evaporator to achieve an even film on the vessel.

Before immunization, the polypeptides of the invention can also be coupled or conjugated to carrier proteins such as tetanus toxin, diphtheria toxin, hepatitis B virus surface antigen, poliomyelitis virus VP1 antigen or any other viral or bacterial toxin or antigen or any suitable proteins to stimulate the development of a stronger immune response. This coupling or conjugation can be done chemically or genetically. A more detailed description of peptide-carrier conjugation is available in Van Regenmortel, M. H. V., Briand J. P., Muller S., Plaué S., <<Synthetic Polypeptides as antigens>> in Laboratory Techniques in Biochemistry and Molecular Biology, Vol. 19 (ed.) Burdou, R. H. & Van Knippenberg P. H. (1988), Elsevier New York.

According to another aspect, there are provided pharmaceutical compositions comprising one or more *Pseudomonas* polypeptides of the invention in a mixture with a pharmaceutically acceptable adjuvant. Suitable adjuvants include (1) oil-in-water emulsion formulations such as MF59™, SAF™, Ribi™; (2) Freund's complete or incomplete adjuvant; (3) salts i.e. $AlK(SO_4)_2$, $AlNa(SO_4)_2$, $AlNH_4(SO_4)_2$, $Al(OH)_3$, $AlPO_4$, silica, kaolin; (4) saponin derivatives such as Stimulon™ or particles generated therefrom such as ISCOMs (immunostimulating complexes); (5) cytokines such as interleukins, interferons, macrophage colony stimulating factor (M-CSF), tumor necrosis factor (TNF); (6) other substances such as carbon polynucleotides i.e. poly IC and poly AU, detoxified cholera toxin (CTB) and *E. coli* heat labile toxin for induction of mucosal immunity; (7) liposomes. A more detailed description of adjuvants is available in a review by M. Z. I Khan et al. in Pharmaceutical Research, vol. 11, No. 1 (1994) pp2-11, and also in another review by Gupta et al., in Vaccine, Vol. 13, No. 14, pp1263-1276 (1995) and in WO 99/24578. Preferred adjuvants include QuilA™, QS21™, Alhydrogel™ and Adjuphos™.

Pharmaceutical compositions of the invention may be administered parenterally by injection, rapid infusion, nasopharyngeal absorption, dermoabsorption, or buccal or oral.

The term "pharmaceutical composition" is also meant to include antibodies. In accordance with the present invention, there is also provided the use of one or more antibodies having binding specificity for the polypeptides of the present invention for the treatment or prophylaxis of *Pseudomonas* infection and/or diseases and symptoms mediated by *Pseudomonas* infection.

Pharmaceutical compositions of the invention are used for the prophylaxis of *Pseudomonas* infection and/or diseases and symptoms mediated by *Pseudomonas* infection as described in Manual of Clinical Microbiology, P. R. Murray (Ed, in chief), E. J. Baron, M. A. Pfaller, F. C. Tenover and R. H. Yolken. ASM Press, Washington, D.C. seventh edition, 1999, 1773p. and in Campa, M. et al. (Eds.) *Pseudomonas aeruginosa* as an opportunistic pathogen (1993) Plenum Press, NY, 419 p.

In one embodiment, pharmaceutical compositions of the present invention are used for the treatment or nosocomial infections, especially in immunocompromised individuals such as ventilator-associated pneumonia in intubated patients, bacteremia in burned patients, chronical infection in cystic fibrosis patients and septicemia. In one embodiment, pharmaceutical compositions of the invention are used for the treatment or prophylaxis of *Pseudomonas* infection and/or diseases and symptoms mediated by *Pseudomonas* infection. In a further embodiment, the *Pseudomonas* infection is mediated by *Pseudomonas aeruginosa*. In a further embodiment, the *Pseudomonas* infection is mediated by *Pseudomonas stutzeri*.

In a particular embodiment, pharmaceutical compositions are administered to those hosts at risk of *Pseudomonas* infection such as infants, elderly and immunocompromised hosts and also hospitalized patients, cystic fibrosis patients, people susceptible to be burnt such as firemen, military personnel.

As used in the present application, the term "host" includes mammals. In a further embodiment, the mammal is human.

Pharmaceutical compositions are preferably in unit dosage form of about 0.001 to 100 µg/kg (antigen/body weight) and more preferably 0.01 to 10 µg/kg and most preferably 0.1 to 1 µg/kg 1 to 3 times with an interval of about 1 to 6 week intervals between immunizations.

Pharmaceutical compositions are preferably in unit dosage form of about 0.1 µg to 10 mg and more preferably 1 µg to 1 mg and most preferably 10 to 100 µg 1 to 3 times with an interval of about 1 to 6 week intervals between immunizations.

According to another aspect, there are provided polynucleotides encoding polypeptides characterized by the amino acid sequence comprising a sequence chosen from SEQ ID NOs: 2, 4, 6, 8, 10, 12 or fragments or analogs thereof.

In one embodiment, polynucleotides are those illustrated in SEQ ID Nos: 1, 3, 5, 7, 9, 11 which may include the open reading frames (ORF), encoding the polypeptides of the invention.

It will be appreciated that the polynucleotide sequences illustrated in the figures may be altered with degenerate codons yet still encode the polypeptides of the invention. Accordingly the present invention further provides polynucleotides which hybridize to the polynucleotide sequences herein above described (or the complement sequences thereof) having 70% identity between sequences. In one embodiment, at least 80% identity between sequences. In one embodiment, at least 85% identity between sequences. In one embodiment, at least 90% identity between sequences. In a further embodiment, polynucleotides are hybridizable under stringent conditions i.e. having at least 95% identity. In a further embodiment, more than 97% identity. Suitable stringent conditions for hybridation can be readily determined by one of skilled in the art (see for example Sambrook et al., (1989) Molecular cloning: A Laboratory Manual, $2^{nd}$ ed, Cold Spring Harbor, N.Y.; Current Protocols in Molecular Biology, (1999) Edited by Ausubel F. M. et al., John Wiley & Sons, Inc., N.Y.).

In a further embodiment, the present invention provides polynucleotides that hybridize under stringent conditions to either
(a) a DNA sequence encoding a polypeptide or
(b) the complement of a DNA sequence encoding a polypeptide;

wherein said polypeptide comprises a sequence chosen from SEQ ID NOS: 2, 4, 6, 8, 10, 12 or fragments or analogs thereof.

In a further embodiment, the present invention provides polynucleotides that hybridize under stringent conditions to either
(a) a DNA sequence encoding a polypeptide or
(b) the complement of a DNA sequence encoding a polypeptide;

wherein said polypeptide comprises at least 10 contiguous amino acid residues from a polypeptide comprising a sequence chosen from SEQ ID NOS: 2, 4, 6, 8, 10, 12 or fragments or analogs thereof.

In a further embodiment, the present invention provides polynucleotides that hybridize under stringent conditions to either
(a) a DNA sequence encoding a polypeptide or
(b) the complement of a DNA sequence encoding a polypeptide;

wherein said polypeptide comprises at least 10 contiguous amino acid residues from a polypeptide comprising a sequence chosen from SEQ ID NOS: 2, 4, 6, 8, 10, 12 or fragments or analogs thereof.

In a further embodiment, the present invention provides polynucleotides that hybridize under stringent conditions to either
(a) a DNA sequence encoding a polypeptide or
(b) the complement of a DNA sequence encoding a polypeptide;

wherein said polypeptide comprises at least 10 contiguous amino acid residues from a polypeptide comprising a sequence chosen from SEQ ID NOS: 2, 4, 6, 8, 10 or 12.

In a further embodiment, polynucleotides are those encoding polypeptides of the invention illustrated in SEQ ID NOS: 2, 4, 6, 8, 10, 12.

In a further embodiment, polynucleotides are those illustrated in SEQ ID NOS: 1, 3, 5, 7, 9, 11 encoding polypeptides of the invention.

As will be readily appreciated by one skilled in the art, polynucleotides include both DNA and RNA.

The present invention also includes polynucleotides complementary to the polynucleotides described in the present application.

According to another aspect, there is provided a process for producing polypeptides of the invention by recombinant techniques by expressing a polynucleotide encoding said polypeptide in a host cell and recovering the expressed polypeptide product. Alternatively, the polypeptides can be produced according to established synthetic chemical techniques i.e. solution phase or solid phase synthesis of oligopeptides which are ligated to produce the full polypeptide (block ligation).

General methods for obtention and evaluation of polynucleotides and polypeptides are described in the following references: Sambrook et al, Molecular Cloning: A Laboratory Manual, 2nd ed, Cold Spring Harbor, N.Y., 1989; Current Protocols in Molecular Biology, Edited by Ausubel F. M. et al., John Wiley and Sons, Inc. New York; PCR Cloning Protocols, from Molecular Cloning to Genetic Engineering, Edited by White B. A., Humana Press, Totowa, N.J. 1997, 490 pages; Protein Purification, Principles and Practices, Scopes R. K., Springer-Verlag, New York, 3rd Edition, 1993, 380 pages; Current Protocols in Immunology, Edited by Coligan J. E. et al., John Wiley & Sons Inc., New York.

The present invention provides host cells transfected with vectors comprising the polynucleotides of the invention.

The present invention provides a process for producing a polypeptide comprising culturing a host cell of the invention under conditions suitable for expression of said polypeptide.

For recombinant production, host cells are transfected with vectors which encode the polypeptides of the invention, and then cultured in a nutrient media modified as appropriate for activating promoters, selecting transformants or amplifying the genes. Suitable vectors are those that are viable and replicable in the chosen host and include chromosomal, non-chromosomal and synthetic DNA sequences e.g. bacterial plasmids, phage DNA, baculovirus, yeast plasmids, vectors derived from combinations of plasmids and phage DNA. The polypeptide sequence may be incorporated in the vector at the appropriate site using restriction enzymes such that it is operably linked to an expression control region comprising a promoter, ribosome binding site (consensus region or Shine-Dalgarno sequence), and optionally an operator (control element). One can select individual components of the expression control region that are appropriate for a given host and vector according to established molecular biology principles (Sambrook et al, Molecular Cloning: A Laboratory Manual, 2nd ed, Cold Spring Harbor, N.Y., 1989; Current Protocols in Molecular Biology, Edited by Ausubel F. M. et al., John Wiley and Sons, Inc. New York). Suitable promoters include but are not limited to LTR or SV40 promoter, *E. coli* lac, tac or trp promoters and the phage lambda $P_L$ promoter. Vectors will preferably incorporate an origin of replication as well as selection markers i.e. ampicilin resistance gene. Suitable bacterial vectors include pET, PQE70, pQE60, pQE-9, pD10 phagescript, psiX174, pbluescript SK, pbsks, pNH8A, pNH16a, pNH18A, pNH46A, ptrc99a, pKK223-3, pKK233-3, pDR540, pRIT5 and eukaryotic vectors pBlueBacIII, pWLNEO, pSV2CAT, pOG44, pXT1, pSG, pSVK3, pBPV, pMSG and pSVL. Host cells may be bacterial i.e. *E. coli*, *Bacillus subtilis, Streptomyces;* fungal i.e. *Aspergillus niger, Aspergillus nidulins;* yeast i.e. *Saccharomyces* or eukaryotic i.e. CHO, COS.

Upon expression of the polypeptide in culture, cells are typically harvested by centrifugation then disrupted by physical or chemical means (if the expressed polypeptide is not secreted into the media) and the resulting crude extract retained to isolate the polypeptide of interest. Purification of the polypeptide from culture media or lysate may be achieved by established techniques depending on the properties of the polypeptide i.e. using ammonium sulfate or ethanol precipitation, acid extraction, anion or cation exchange chromatography, phosphocellulose chromatography, hydrophobic interaction chromatography, hydroxylapatite chromatography and lectin chromatography. Final purification may be achieved using HPLC.

The polypeptides may be expressed with or without a leader or secretion sequence. In the former case the leader may be removed using post-translational processing (see U.S. Pat. Nos. 4,431,739; 4,425,437; and 4,338,397) or be chemically removed subsequent to purifying the expressed polypeptide.

According to a further aspect, the *Pseudomonas* polypeptides of the invention may be used in a diagnostic test for *Pseudomonas* infection, in particular *Pseudomonas aeruginosa* infection.

Several diagnostic methods for *Pseudomonas* infection in an host susceptible to *Pseudomonas* infection are possible, for example detecting *Pseudomonas* organism in a biological sample, the following procedure may be followed:

a) obtaining a biological sample from a host;
b) incubating an antibody or fragment thereof reactive with a *Pseudomonas* polypeptide of the invention with the biological sample to form a mixture; and
c) detecting specifically bound antibody or bound fragment in the mixture which indicates the presence of *Pseudomonas*.

Alternatively, a method for diagnostic for *Pseudomonas* infection in an host susceptible to *Pseudomonas* infection includes a method for the detection of antibody specific to a *Pseudomonas* antigen in a biological sample containing or suspected of containing said antibody may be performed as follows:

a) obtaining a biological sample from a host;
b) incubating one or more *Pseudomonas* polypeptides of the invention or fragments thereof with the biological sample to form a mixture; and
c) detecting specifically bound antigen or bound fragment in the mixture which indicates the presence of antibody specific to *Pseudomonas*.

One of skill in the art will recognize that this diagnostic test may take several forms, including an immunological test such as an enzyme-linked immunosorbent assay (ELISA), a radioimmunoassay or a latex agglutination assay, essentially to determine whether antibodies specific for the polypeptide are present in an organism.

The DNA sequences encoding polypeptides of the invention may also be used to design DNA probes for use in detecting the presence of *Pseudomonas* in a biological sample suspected of containing such bacteria. The detection method of this invention comprises:

a) obtaining the biological sample from a host;
b) incubating one or more DNA probes having a DNA sequence encoding a polypeptide of the invention or fragments thereof with the biological sample to form a mixture; and
c) detecting specifically bound DNA probe in the mixture which indicates the presence of *Pseudomonas* bacteria.

The DNA probes of this invention may also be used for detecting circulating *Pseudomonas* i.e. *Pseudomonas* nucleic acids in a sample, for example using a polymerase chain reaction, as a method of diagnosing *Pseudomonas* infections. The probe may be synthesized using conventional techniques and may be immobilized on a solid phase, or may be labelled with a detectable label. A preferred DNA probe for this application is an oligomer having a sequence complementary to at least about 6 contiguous nucleotides of the *Pseudomonas* polypeptides of the invention. In a further embodiment, the preferred DNA probe will be an oligomer having a sequence complementary to at least about 15 contiguous nucleotides of the *Pseudomonas* polypeptides of the invention. In a further embodiment, the preferred DNA probe will be an oligomer having a sequence complementary to at least about 30 contiguous nucleotides of the *Pseudomonas* polypeptides of the invention. In a further embodiment, the preferred DNA probe will be an oligomer having a sequence complementary to at least about 50 contiguous nucleotides of the *Pseudomonas* polypeptides of the invention.

Another diagnostic method for the detection of *Pseudomonas* in a host comprises:
a) labelling an antibody reactive with a polypeptide of the invention or fragment thereof with a detectable label;
b) administering the labelled antibody or labelled fragment to the host; and
c) detecting specifically bound labelled antibody or labelled fragment in the host which indicates the presence of *Pseudomonas*.

In a further aspect, polynucleotides encoding polypeptides of the invention, or fragments, analogs or derivatives thereof, may be used in a DNA immunization method. That is, they can be incorporated into a vector which is replicable and expressible upon injection thereby producing the antigenic polypeptide in vivo. For example polynucleotides may be incorporated into a plasmid vector under the control of the CMV promoter which is functional in eukaryotic cells. Preferably the vector is injected intramuscularly.

A further aspect of the invention is the use of the *Pseudomonas* polypeptides of the invention as immunogens for the production of specific antibodies for the diagnosis and in particular the treatment of *Pseudomonas* infection.

A further aspect of the invention is the use of the antibodies directed to the polypeptides of the invention for passive immunization, whereby an antibody raised by a polypeptide of the invention is administered to a host in an amount sufficient to provide a passive immunization. One could use the antibodies described in the present application. Suitable antibodies may be determined using appropriate screening methods, for example by measuring the ability of a particular antibody to passively protect against *Pseudomonas* infection in a test model. One example of an animal model is the mouse model described in the examples herein. The antibody may be a whole antibody or an antigen-binding fragment thereof and may belong to any immunoglobulin class. The antibody or fragment may be of animal origin, specifically of mammalian origin and more specifically of murine, rat or human origin. It may be a natural antibody or a fragment thereof, or if desired, a recombinant antibody or antibody fragment. The term recombinant antibody or antibody fragment means antibody or antibody fragment which was produced using molecular biology techniques. The antibody or antibody fragments may be polyclonal, or preferably monoclonal. It may be specific for a number of epitopes associated with the *Pseudomonas* polypeptides but is preferably specific for one.

The use of a polynucleotide of the invention in genetic immunization will preferably employ a suitable delivery method or system such as direct injection of plasmid DNA into muscles [Wolf et al. H M G (1992) 1: 363; Turnes et al., Vaccine (1999), 17: 2089; Le et al., Vaccine (2000) 18: 1893; Alves et al., Vaccine (2001) 19: 788], injection of plasmid DNA with or without adjuvants [Ulmer et al., Vaccine (1999) 18: 18; MacLaughlin et al., J. Control Release (1998) 56: 259; Hartikka et al., Gene Ther. (2000) 7: 1171-82; Benvenisty and Reshef, PNAS USA (1986) 83:9551; Singh et al., PNAS USA (2000) 97: 811], targeting cells by delivery of DNA complexed with specific carriers [Wa et al., J Biol Chem (1989) 264: 16985; Chaplin et al., Infect. Immun. (1999) 67: 6434], injection of plasmid complexed or encapsulated in various forms of liposomes [Ishii et al., AIDS Research and Human Retroviruses (1997) 13: 142; Perrie et al., Vaccine (2001) 19: 3301], administration of DNA with different methods of bombardment [Tang et al., Nature (1992) 356: 152; Eisenbraun et al., DNA Cell Biol (1993) 12: 791; Chen et al., Vaccine (2001) 19: 2908], and administration of DNA with lived vectors [Tubulekas et al., Gene (1997) 190: 191; Pushko et al., Virology (1997) 239: 389; Spreng et al. FEMS (2000) 27: 299; Dietrich et al., Vaccine (2001) 19: 2506].

In a further aspect, the invention provides a method for prophylactic or therapeutic treatment of *Pseudomonas* infection in a host susceptible to *Pseudomonas* infection comprising administering to the host a prophylactic or therapeutic amount of a pharmaceutical composition of the invention.

In a further embodiment, the invention provides the use of a pharmaceutical composition of the invention in the manufacture of a medicament for the prophylactic or therapeutic treatment of *Pseudomonas* infection.

In a further embodiment, the invention provides a kit comprising a polypeptide of the invention for detection or diagnosis of *Pseudomonas* infection.

Unless otherwise defined, all technical and scientific terms used herein have the same meaning as commonly understood by one of ordinary skill in the art to which this invention belongs. All publications, patent applications, patents, and other references mentioned herein are incorporated by reference in their entirety. In case of conflict, the present specification, including definitions, will control. In addition, the materials, methods, and examples are illustrative only and not intended to be limiting.

EXAMPLE 1

This example illustrates the cloning and molecular characteristics of SPA-1 gene and corresponding polypeptide.

The coding region of *P. aeruginosa* SPA-1 (SEQ ID NO: 1) gene was amplified by PCP (Hybaid PCR Express, ESBE Scientific, Markham, Ontario, Canada) from genomic DNA of *P. aeruginosa* strain PAO1 using the following oligos that contained base extensions for the addition of restriction sites NdeI (CATATG) and NotI (GCGGCCGC): PSEU59 (5'-GG-GAATTCCATATGGCGCAGAAGAATCCGACAGTCG-3') (SEQ ID NO:7) and PSEU60 (5'-ATAAGAATGCGGC-CGCTGGCGTCCGCAGGCGGT-3') (SEQ ID NO:8). PCR products were purified from agarose gel using a QIAquick gel extraction kit following the manufacturer's instructions (Qiagen, Chatsworth, Calif.), and digested with NdeI and NotI (Amersham Pharmacia Biotech, Inc, Baie d'Urfé, Canada). The pET21b(+) vector (Novagen, Madison, Wis.) was digested with NdeI and NotI and purified from agarose gel using a QIAquick gel extraction kit (Qiagen). The NdeI-NotI PCR products were ligated to the NdeI-NotI pET21b(+) expression vector. The ligated products were transformed into *E. coli* strain DH5α [φ80dlacZΔM15 Δ(lacZYA-argF) U169 endA1 recA1 hsdR17($r_k$-$m_k$+) deoR thi-1 supE44 λ⁻gyrA96 relA1] (Gibco BRL, Gaithersburg, Md.) according to the method of Simanis (Hanahan, D. DNA Cloning, 1985, D. M. Glover (ed), pp. 109-135). Recombinant pET21b(+) plasmid (rpET21b(+)) containing SPA-1 gene was purified using a Qiagen kit and DNA insert was sequenced (Taq Dye Deoxy Terminator Cycle Sequencing kit, ABI, Foster City, Calif.).

TABLE 1

Oligonucleotide primers used for PCR amplification of P. aeruginosa genes.

| Genes | Primers I.D. | Restriction site | Vector | Sequence | Sequence I.D. No. |
|---|---|---|---|---|---|
| SPA-1 | PSEU59 | NdeI | pET21b (+) | 5'-GGGAATTCCATATGGCGCAGA AGAATCCGACAGTCG-3' | 7 |
| SPA-1 | PSEU60 | NotI | pET21b(+) | 5'-ATAAGAATGCGGCCGCTCGCG TCCGCAGGCGGT-3' | 8 |
| SPA-1 | PSEU409 | BglII | pCMV-GH | 5'-GGGCAGATCTTGATGGCGCAG AAGAATCCG-3' | 9 |
| SPA-1 | PSEU410 | XbaI | pCMV-GH | 5'-GATCCTCTAGATTGGCGTCCG CAGGCGGTC-3' | 10 |
| SPA-2 | PSEU47 | NdeI | pET21b (+) | 5'-GGGAATTCCATATGGGCTTCC AACTGCGCGG-3' | 11 |
| SPA-2 | PSEU48 | HindIII | PET21b (+) | 5'-CGCCAAGCTTCGGGGTGGGGA ACTCGAT-3' | 12 |
| SPA-2 | PSEU411 | BamHI | pCMV-GH | 5'-CGAGGATCCTATGTGCGGCTT CCAACTGCG-3' | 13 |
| SPA-2 | PSEU412 | HindIII | pCMV-GH | 5'-CAGAAGCTTCGGGGTGGGGAA CTCGATCGGC-3' | 14 |
| SPA-3 | PSEU37 | NdeI | pET21b (+) | 5'-GGGAATTCCATATGAGCAGCA ACAGCAAGAAGGAACTC-3' | 15 |
| SPA-3 | PSEU38 | HindIII | pET21b (+) | 5'-CGCCAAGCTTGCGGATGGTGT AGGCGAC-3' | 16 |
| SPA-3 | PSEU413 | BamHI | pCMV-GH | 5'-CGAGGATCCTATGAGCAAGAA GGAACTCCC-3' | 17 |
| SPA-3 | PSEU414 | HindIII | pCMV-GH | 5'-CAGAAGCTTCTAGCGGATTGG TGTAGGCGAC-3' | 18 |

It was determined that the open reading frame (ORF) which codes for SPA-1 polypeptide contains 1347 bp and encodes a 448 amino acid residues polypeptide with a predicted pI of 8.20 and a predicted molecular mass of 47757.95 Da. Analysis of the predicted amino acid residues sequence (SEQ ID NO:2) using the Spscan software (Wisconsin Sequence Analysis Package; Genetics Computer Group) suggested the existence of a 32 amino acid residues signal peptide (MRNPERSALLKVSGLLGSTVVAMGLGLSSACA) (SEQ ID NO:37), which ends with a cleavage site located between an alanine and a glutamine residues.

To confirm the presence by PCR amplification of SPA-1 (SEQ ID NO:1) gene, the following 5 distinct P. aeruginosa strains were used: P. aeruginosa PAO1, NF25, NF45, 1019-5 and B. Clinical isolates were provided by the Centre de Recherche en Infectiologie (Laval University, Québec, Canada). The E. coli XL1-Blue MRF' was used in these experiments as a negative control. SPA-1 (SEQ ID NO:1) gene was amplified by PCR (Hybaid PCR Express, ESBE Scientific) from genomic DNA from the 5 P. aeruginosa strains, and the control E. coli strain using the oligonucleotides primers PSEU59 and PSEU60 (Table 1). PCR was performed with 10 cycles of 10 sec at 94° C., 30 sec at 45° C. and 2 min at 68° C. followed by 20 cycles of 10 sec at 94° C., 30 sec at 45° C. and 2 min with 0.05 sec increments per cycle at 68° C. and a final elongation period of 7 min at 68° C. The PCR products were size fractionated in 1% agarose gels and were visualized by ethidium bromide staining. The results of these PCR amplifications are presented in Table 2. The analysis of the amplification products revealed that SPA-1 (SEQ ID NO:1) gene was present in the genome of all of the 5 P. aeruginosa strains tested. No such product was detected when the control *E. coli* DNA was submitted to identical PCR amplifications with these oligonucleotide primers.

TABLE 2

Identification of *P. aeruginosa* genes by PCR amplification.

| Strain Identification | Identification by PCR amplification of | | |
|---|---|---|---|
| | SPA-1 | SPA-2 | SPA-3 |
| PAO1 | + | + | + |
| NF25 | + | + | + |
| NF45 | + | + | + |
| 1019-5 | + | + | + |
| B | + | + | + |
| *E. coli* | − | − | − |

EXAMPLE 2

This example illustrates the cloning and molecular characteristics of SPA-2 gene and corresponding polypeptide.

The coding region of *P. aeruginosa* SPA-2 (SEQ ID NO: 3) gene was amplified by PCR (Hybaid PCR Express, ESBE Scientific) from genomic DNA of *P. aeruginosa* strain PAO1 using the following oligos that contained base extensions for the addition of restriction sites NdeI (CATATG) and HindIII (AAGCTT): PSEU47 and PSEU48, which are presented in Table 1. The methods used for cloning SPA-2 gene into an expression vector and sequencing are similar to the methods described in Example 1.

It was determined that the open reading frame (ORF) which codes for SPA-2 contains 624 bp and encodes a 207 amino acid residues polypeptide with a predicted pI of 5.04 and a predicted molecular mass of 22882.24 Da. Analysis of the predicted amino acid residues sequence (SEQ ID NO:4) using the Spscan software (Wisconsin Sequence Analysis Package; Genetics Computer Group) suggested the existence of a 19 amino acid residues signal peptide (MKRILTSAALIGMTTLLAA) (SEO ID NO:38), which ends with a cleavage site located between an alanine and a cysteine residues.

The SPA-2 gene was shown to be present after PCR amplification using the oligonucleotide primers PSEU47 and PSEU48 in the 5 *P. aeruginosa* strains tested (Table 2). The methods used for PCR amplification of the SPA-2 gene were similar to the methods presented in Example 1. No such product was detected when the control *E. coli* DNA was submitted to identical PCR amplification with these oligonucleotide primers.

EXAMPLE 3

This example illustrates the cloning and molecular characteristics of SPA-3 gene and corresponding polypeptide.

The coding region of *P. aeruginosa* SPA-3 (SEQ ID NO: 5) gene was amplified by PCR (Hybaid PCR Express, ESBE Scientific) from genomic DNA of *P. aeruginosa* strain PAO1 using the following oligos that contained base extensions for the addition of restriction sites NdeI (CATATG) and HindIII (AAGCTT): PSEU37 and PSEU38, which are presented in Table 1. The methods used for cloning SPA-3 gene into an expression vector and sequencing are similar to the methods described in Example 1.

It was determined that the open reading frame (ORF) which codes for SPA-3 contains 1143 bp and encodes a 380 amino acid residues polypeptide with a predicted pI of 5.15 and a predicted molecular mass of 40394.19 Da. Analysis of the predicted amino acid residues sequence (SEQ ID NO:6) using the Spscan software (Wisconsin Sequence Analysis Package; Genetics Computer Group) suggested the existence of a 21 amino acid residues signal peptide (MVQWKHAALLALALAVVGCSS) (SEQ ID NO:39), which ends with a cleavage site located between a serine and an asparagine residues.

The SPA-3 gene was shown to be present after PCR amplification using the oligonucleotide primers PSEU37 and PSEU38 in the 5 *P. aeruginosa* strains tested (Table 2). The methods used for PCR amplification of the SPA-3 gene were similar to the methods presented in Example 1. No such product was detected when the control *E. coli* DNA was submitted to identical PCR amplification with these oligonucleotide primers.

EXAMPLE 4

This example illustrates the cloning of *P. aeruginosa* genes in CMV plasmid pCMV-GH.

The DNA coding regions of *P. aeruginosa* polypeptides are inserted in phase downstream of a human growth hormone (hGH) gene which is under the transcriptional control of the cytomegalovirus (CMV) promotor in the plasmid vector pCMV-GH (Tang et al., Nature, 1992, 356:152). The CMV promotor is non-functional in *E. coli* cells but active upon administration of the plasmid in eukaryotic cells. The vector also incorporates the ampicillin resistance gene.

The coding regions of SPA-1 (SEQ ID NO: 1), SPA-2 (SEQ ID NO: 3) and SPA-3 (SEQ ID NO: 5) genes without their leader peptide regions are amplified by PCR (Hybaid PCR Express, ESBE Scientific) from genomic DNA of *P. aeruginosa* strain PAO1 using oligonucleotide primers that contained base extensions for the addition of restriction sites BamHI (GGATCC), BglII (AGATCT), XbaI (TCTAGA), or HindIII (AAGCTT) which are described in Table 1. The PCR products are purified from agarose gel using a QIAquick gel extraction kit (Qiagen), and digested with restriction enzymes (Amersham Pharmacia Biotech, Inc). The pCMV-GH vector (Laboratory of Dr. Stephen A. Johnston, Department of Biochemistry, The University of Texas, Dallas, Tex.) is digested with BamHI, BglII, XbaI, or HindIII and purified from agarose gel using the QIAquick gel extraction kit (Qiagen). The digested DNA fragments are ligated to the digested pCMV-GH vector to create the hGH-SPA-1, hGH-SPA-2 and hGH-SPA-3 fusion polypeptides under the control of the CMV promoter. The ligated products are transformed into *E. coli* strain DH5α [φ80dlacZΔM15 Δ(lacZYA-argF) U169 endA1 recA1 hsdR17($r_k$-$m_k$+) deoR Thi-1 supE44 λ⁻gyrA96 relA1] (Gibco BRL) according to the method of Simanis (Hanahan, D. DNA Cloning, 1985, D. M. Glover (ed), pp. 109-135). The recombinant pCMV plasmids are purified using a Qiagen kit, and the nucleotide sequences of the DNA inserts are verified by DNA sequencing.

EXAMPLE 5

This example illustrates the use of DNA to elicit an immune response to *P. aeruginosa* polypeptide antigens.

A group of 8 female BALB/c mice (Charles River, St-Constant, Qubéc, Canada) are immunized by intramuscular injection of 100 µl three times at two- or three-week intervals with 50 µg of recombinant pCMV-GH encoding SPA-1 (SEQ ID NO: 1), SPA-2 (SEQ ID NO: 3) and SPA-3 (SEQ ID NO: 5) genes in presence of 50 µg of granulocyte-macrophage colony-stimulating factor (GM-CSF)-expressing plasmid pCMV-GH-GM-CSF (Laboratory of Dr. Stephen A.

Johnston, Department of Biochemistry, The University of Texas, Dallas, Tex.). As control, a group of mice are injected with 50 μg of pCMV-GH in presence of 50 μg of pCMV-GH-GM-CSF. Blood samples are collected from the orbital sinus prior to each immunization and seven days following the third injection. Serum antibody responses are determined by ELISA using the corresponding His-Tag labeled *P. aeruginosa* recombinant polypeptides as coating antigen. The production and purification of these His-tag labeled *P. aeruginosa* recombinant polypeptides are presented in Example 6.

EXAMPLE 6

This example illustrates the production and purification of *P. aeruginosa* recombinant polypeptides.

The recombinant pET21b(+) plasmid with SPA-1 (SEQ ID NO: 1), SPA-2 (SEQ ID NO: 3) and SPA-3 (SEQ ID NO: 5) genes were used to transform by electroporation (Gene Pulser II apparatus, BIO-RAD Labs, Mississauga, Canada) *E. coli* strain Tuner (DE3) [F⁻ ompt hsdS$_B$ (r$_B^-$ m$_B^-$) gal dcm lacY1 (DE3)] (Novagen). In this strain of *E. coli*, the T7 promotor controlling expression of the recombinant polypeptide is specifically recognized by the T7 RNA polymerase (present on the λDE3 prophage) whose gene is under the control of the lac promotor which is inducible by isopropyl-β-d-thio-galacto-pyranoside (IPTG). The transformant Tuner(DE3)/rpET21 was grown at 37° C. with agitation at 250 rpm in Luria-Betani (LB) broth (peptone 10 g/L, yeast extract 5 g/L, NaCl 10 g/L) containing 100 μg of ampicillin (Sigma-Aldrich Canada Ltd., Oakville, Canada) per ml until the A$_{600}$ reached a value of 0.5. In order to induce the production of His-tagged *P. aeruginosa* recombinant polypeptides, the cells were incubated for 3 additional hours in the presence of IPTG at a final concentration of 1 mM. Induced cells from a 1-L culture were pelleted by centrifugation and frozen at −70° C.

The purification of the recombinant polypeptides from the soluble or insoluble cytoplasmic fractions of IPTG-induced Tuner(DE3)/rpET21 was done by affinity chromatography based on the properties of the His.Tag sequence (6 consecutive histidine residues) to bind to divalent cations (Ni$^{2+}$) immobilized on the His•Bind metal chelation resin. Briefly, for the purification of SPA-2 and SPA-3 polypeptides from the soluble cytoplasmic fraction, the pelleted cells obtained from a 1-L culture induced with IPTG were sonicated and centrifuged at 21,000×g for 30 min to remove debris. For the purification of recombinant polypeptides SPA-1 from the insoluble cytoplasmic fraction, the cells were sonicated and centrifuged as above and the resulting pellet was resuspended in lysis buffer (5 mM imidazole, 2 M NaCl, 20 mM Tris-HCl pH 7.9) with 6 M Guanidine-HCl. The suspension was incubated on ice for 1 h and centrifuged at 39,000×g for 20 min. The supernatants containing soluble SPA-2 and SPA-3 polypeptides or solubilized SPA-1 polypeptide were deposited on a Ni-NTA agarose column (Qiagen). The His-tag labeled *P. aeruginosa* recombinant polypeptides were eluted with 250 mM imidazole-500 mM NaCl-20 mM Tris pH 7.9. The removal of the salt and imidazole from the sample was done by dialysis against PBS at 4° C. The quantities of recombinant polypeptides obtained from the soluble or insoluble fractions of *E. coli* was estimated by MicroBCA (Pierce, Rockford, Ill.).

EXAMPLE 7

This example illustrates the reactivity of the His-tagged *P. aeruginosa* recombinant polypeptides with antibodies present in human sera.

As shown in Table 3, SPA-1, SPA-2 and SPA-3 His-tagged recombinant polypeptides were recognized in immunoblots by the antibodies present in the human sera. It indicates that humans, which are normally in contact with *P. aeruginosa*, do develop antibodies that are specific to these polypeptides. These particular human antibodies might be implicated in the protection against *P. aeruginosa* infection.

TABLE 3

Reactivity in immunoblots of antibodies present in human sera with *P. aeruginosa* His-tagged fusion recombinant polypeptides.

| Purified recombinant polypeptide I.D.[1] | Apparent molecular weight (kDa)[2] | Reactivity in immunoblots with antibodies present in human sera[3] |
|---|---|---|
| SPA-1 | 48 | + |
| SPA-2 | 25 | + |
| SPA-3 | 40 | + |

[1]His-tagged recombinant polypeptides produced and purified as described in Example 6 were used to perform the immunoblots.
[2]Molecular weight of the His-tagged recombinant polypeptide was estimated after SDS-PAGE.
[3]A pool of three human sera, each diluted 1/500, was prepared in order to perform the immunoblots.

EXAMPLE 8

This example illustrates the accessibility to antibodies of the SPA-1, SPA-2 and SPA-3 polypeptides at the surface of *P. aeruginosa* strain.

Bacteria were grown overnight on blood agar at 30° C. Colonies were resuspended in LB broth to obtain an O.D.$_{60\,nm}$ of 0.3. Dilutions of anti-SPA-1, anti-SPA-2 or anti-SPA-3 or control sera were then added and allowed to bind to the cells, which were incubated for 2 h at 4° C. with rotation. Samples were washed 2 times in blocking buffer [phosphate-buffered saline (PBS) containing 2% bovine serum albumin (BSA)], and then 500 μl of goat fluorescein (FITC)-conjugated anti-mouse IgG Fc (gamma) fragment-specific, diluted in blocking buffer, was added. After an additional incubation of 2 h at 4° C. with rotation in the dark, samples were washed 2 times in blocking buffer and fixed with 0.25 % formaldehyde in PBS buffer for 18 h at 4° C. Cells were centrifuged and resuspended in 0.5 ml of PBS buffer. Cells were kept in the dark at 4° C. until analyzed by flow cytometry (Epics® XL; Beckman Coulter, Inc.). Flow cytometric analysis revealed that SPA-1-, SPA-2-, and SPA-3-specific antibodies efficiently recognized their corresponding surface-exposed epitopes on the homologous (PAO1) *P. aeruginosa* strain tested (Table 4). It was determined that more than 55 % of the 10,000 *Pseudomonas* cells analyzed were labeled with the antibodies present in the SPA-1-, SPA-2-, and SPA-3-specific sera. These observations clearly demonstrate that the SPA-1, SPA-2 and SPA-3 polypeptides are accessible at the surface, where they can be easily recognized by antibodies. Anti-*P. aeruginosa* antibodies were shown to play an important role in the protection against *P. aeruginosa* infection.

TABLE 4

Evaluation of the attachment of SPA-1-, SPA-2- and SPA-3-specific antibodies at the surface of intact cells of *P. aeruginosa* strain PAO1.

| Serum Identification | Fluorescence Index[2] | % of labeled cells[3] |
|---|---|---|
| SPA-1-specific sera[1] | 10.0 | 58 |
| SPA-2-specific sera | 21.3 | 75 |

TABLE 4-continued

Evaluation of the attachment of SPA-1-, SPA-2- and SPA-3-specific antibodies at the surface of intact cells of *P. aeruginosa* strain PAO1.

| Serum Identification | Fluorescence Index[2] | % of labeled cells[3] |
|---|---|---|
| SPA-3-specific sera | 10.0 | 55 |
| Negative control sera[4] | 1.0 | 1.0 |
| Positive control serum[5] | 37.4 | 83 |

[1]Mice were injected subcutaneously four times at two-week intervals with 20 μg of purified recombinant polypeptides mixed with 10 μg of QuilA adjuvant (Cedarlane Laboratories, Hornby, Canada). Sera were diluted 1/50.
[2]The fluorescence index was calculated as the median fluorescence value obtained after labeling the cells with an immune serum divided by the fluorescence value obtained for a control mouse serum. A fluorescence value of 1 indicated that there was no binding of antibodies at the surface of intact *Pseudomonas* cells.
[3]% of labeled cells out of the 10,000 cells analyzed.
[4]Sera collected from unimmunized or sham-immunized mice were pooled, diluted 1/50, and used as negative controls for this assay.
[5]Serum obtained from a mouse immunized with 20 μg of purified recombinant outer membrane polypeptide OprI from *P. aeruginosa* strain PAO1 was diluted 1/50 and used as a positive control for the assay.

EXAMPLE 9

This example illustrates the protection of mice against *P. aeruginosa* infection induced by immunization with SPA-2 recombinant polypeptide.

Groups of 4 female BALB/c mice (Charles River) were immunized subcutaneously four times at two-week intervals with 20 μg of affinity purified His-tagged *P. aeruginosa* SPA-2 recombinant polypeptide in presence of 10% of QuilA adjuvant (Cedarlane Laboratories Ltd) or, as control, with QuilA adjuvant alone in PBS. Blood samples were collected from the orbital sinus on day 0, 14, 28, and 42 prior to each immunization and 7 days (day 49) following the fourth injection. One week later, the mice were challenged intratracheally with approximately $5 \times 10^7$ CFU of *P. aeruginosa* strain PAO1. Samples of the *P. aeructinosa* challenge inoculum were plated on blood agar plates to determine the CFU and to verify the challenge dose. Mice survival was monitored on a 5-day period and protection was reported as the percentage of surviving mice compared to survival in the group of mice immunized with adjuvant only. Results reported in Table 5 indicate that immunization with SPA-2 recombinant polypeptide can delay mortality and protect mice from a lethal *Pseudomonas* infection.

TABLE 5

Protection confered by immunization with SPA-2 recombinant polypeptide against an intratracheal lethal challenge.

| Groups[1] | % Survival | Mean Survival Time |
|---|---|---|
| SPA-2 | 75 | 108 h |
| QuilA | 25 | 75 h |

[1]Mice were injected subcutaneously four times at two-week intervals with 20 μg of purified recombinant polypeptide mixed with 10 μg of QuilA adjuvant (Cedarlane Laboratories, Hornby, Canada); or with QuilA adjuvant only as a negative control.

EXAMPLE 10

This example illustrates the identification of SPA-1 homologs, in the *Pseudomonas aeruginosa* genome, which can be used as immunogens for vaccines.

Genome analysis allowed the identification of 3 genes coding for proteins homologous to SPA-1. The sequences of each gene and protein are presented in FIGS. 7, 9, 11 and FIGS. 8, 10, 12 respectively. SHB-PA104 (SEQ ID No: 8), SHB-PA105 (SEQ ID No: 10) and SHB-PA106 (SEQ ID No: 12) proteins present 49.4% (over 389 aa; FIG. 13), 33.2 % (over 361 aa; FIG. 14) and 32.2% (over 289 aa; FIG. 15) identity with SPA-1 protein (448 aa) respectively. A paper presenting the 4 homologous proteins was published in January 2002 (Blackburn, N. T. and Clarke, A. J. (2002) Biochemistry, 41: 1001-1013). The paper describes these proteins as a family of lytic transglycosylases. Due to homologies with SPA-1, they may represent interesting, accessible vaccine candidates. Table 6 describes primers to amplify the three novel genes that can be overexpressed, purified and used as immunogens as for SPA-1.

TABLE 6

Oligonucleotide primers for PCR amplification of new *P. aeruginosa* genes.

| Genes | Primers I.D. | Restriction site | Vector | Sequence | Sequence I.D. No. |
|---|---|---|---|---|---|
| SHB-PA104 | PSEU446 | NdeI | pET19b | 5'-GAGTTCCATATGAGCTTCCCTTCCTGCCTCGCCGGCCTGCAG-3' | 25 |
| SHB-PA104 | PSEU622 | BamHI | pET19b | 5'-CGCTGAGGATCCTCACTTCTGCAATTGCTTGCGCTCGAGCC-3' | 26 |
| SHB-PA105 | PSEU442 | NdeI | pET19b | 5'-GGGAATTCCATATGGGGGCGGCCCAGGCGG CG-3' | 27 |
| SHB-PA105 | PSEU443 | BamHI | pET19b | 5'-GCGCTGAGGATCCTCAATGGGCACCTCGCG-3' | 28 |
| SHB-PA106 | PSEU438 | NdeI | pET19b | 5'-GGGAATTCCATATGAGCAGCGAACCGACGC-3' | 29 |

TABLE 6-continued

Oligonucleotide primers for PCR amplification of new *P. aeruginosa* genes.

| Genes | Primers I.D. | Restriction site | Vector | Sequence | Sequence I.D. No. |
|---|---|---|---|---|---|
| SHB-PA106 | PSEU638 | HindIII | pET19b | 5'-CGCCAAGCTTCTAATCCTGCCTGACGACGG-3' | 30 |

EXAMPLE 11

This example illustrates the method used for extracting lipids from bacterial cells.

Complex lipid mixtures are extracted from *E. coli* in order to generate liposome formulations from bacterial origin. To generate such complex lipid mixtures other bacterial species would have also been suitable such as: *Neisseria* spp, *Haemophilus* spp, *Pseudomonas* spp, *Bacteriodes* spp, *Legionella* spp, *Vibrio* spp, *Brucella* spp, *Bordetella* spp, *Campylobacter* spp, *Klebsiella* spp, *Salmonella* spp, *Shigella* spp, *Proteus* spp, and *Yersinia* spp. Other species could also be used. The following method is used to generate the complex lipid mixtures used to generate the liposome formulations presented in Example 12.

Bacteria are grown overnight in BHI broth at 37° C. in presence of 8% $CO_2$ (175 rpm). Cells are collected by centrifugation and the pellet is suspended in 6.7 ml of methanol per gram of cells (wet weight). This bacterial suspension is sonicated in an ice bath twice using a Sonic dismembrator 500 (Fisher Scientific) with a microtip probe adjusted at 8. This suspension is then heated at 65° C. for 30 mm. After this incubation period, 2 volumes of chloroform are added to the suspension and agitated for 1 h at room temperature. The suspension is filtered through Whatman No. 4 filter. The filtrate is transferred in a Teflon tube and 0.2 volume of saline solution (NaCl 0.6% (w/v)) is then added. After centrifugation, the upper phase and the precipitate at the interface are discarded. The lower phase is extracted with one volume of chloroform:methanol:saline solution (3:48:47) at least four times or until there is no more precipitate at the interface. After the final extraction, the lower organic phase is dried in a rotatory evaporator (Rotavapor, Büchi, Switzerland). The dried phospholipids are stored at −80° C. or resuspended in a solution of chloroform:methanol (2:1).

EXAMPLE 12

This example illustrates the incorporation of recombinant SPA-1 into different liposome formulations.

Liposomes are prepared using a dialysis method. Liposomes are prepared with different synthetic (see list 1 in this Example; Other lipids can be used and are described in Remington's on Pharmaceutical Sciences, 18th ed., 1990, Mack Publishing Co., Pennsylvania, p. 390.) or bacterial phospholipids and/or cholesterol, which are combined at different ratios. Some liposome formulations are also prepared with the adjuvant monophosphoryl lipid A (MPLA, Avanti polar lipids, Alabaster, Ala.) at 600 µg/ml. SPA-1 protein is first precipitated in 90% ethanol (vol/vol) and denatured in 1 ml of PBS buffer containing 1% (wt/vol) of SDS (Sigma chemical) in PBS buffer, and heated at 100° C. for 10 min. The solution is diluted with 1 ml of PBS buffer containing 15% (wt/vol) of n-octyl .-D-glucopyranoside (OG, Sigma) and incubated at room temperature for 3 h. Lipids are dissolved in a chloroform:methanol solution (2:1) in a round bottom glass flask and dried using a rotatory evaporator (Rotavapor, Büchi, Switzerland) to achieve an even film on the vessel. The above protein-detergent solution is then added to the lipid film and mixed gently until the film is dissolved. The solution after mixing is slightly opalescent in appearance. The solution is then extensively dialysed against PBS buffer (pH 7.4) to remove detergent and to induce liposome formation. After dialysis, the resulting milky solution is sequentially extruded through 1000, 400, 200, and 100 nm polycarbonate filters using a stainless steel extrusion device (Lipex Biomembranes, Vancouver, Canada). The unencapsulated proteins are removed by ultracentrifugation at 25 0000×g for 1 h at 4° C. The pellet is suspended with PBS buffer containing 0.3 M of sucrose. Vesicle size and homogeneity are evaluated by quasi-elastic light scattering with a submicron particles analyzer (model N4 Plus, Beckman Coulter). Using this apparatus, it is estimated that the liposome size in the different preparations is approximately 100 nm. All liposome preparations are sterilized by filtration through a 0.22-µm membrane and stored at −80° C. until used. The amount of recombinant protein incorporated in the liposome is estimated by MicroBCA (Pierce, Rockford, Ill.) after phospholipid extraction of SPA-1-liposome preparations with chloroform:methanol solution (2:1) as described by Wessel and Flügge (*Anal. Biochem.* 1984, 138:141-143).

Gel filtration is used as an alternate method to induce the formation of SPA-1 liposome from the SPA-1-OG-SDS-lipids mixed micellar solution and to remove detergents. The SPA-1-OG-SDS-lipids solution is applied directly on top of a Sephadex G-50 (column size: 2×20 cm, Pharmacia) or a P-6 (column size: 2×20 cm, Bio Rad) size exclusion chromatography/desalting column and eluted with PBS buffer at a flow rate of 2.5 ml/min.

Fractions containing both protein and lipids are pooled, extruded, centrifuged, and the vesicle sizes are evaluated as described above. All preparations are sterilized through a 0.22-µm membrane and stored at −80° C. until used.

List 1. Partial List of Synthetic Lipids Used to Prepare SPA-1-Liposome Preparations.

1,2-Dilauroyl-sn-Glycero-3-Phosphate (DLPA), Dimyristoyl-sn-Glycero-3-Phosphate (DMPA), 1,2-Dipalmitoyl-sn-Glycero-3-Phosphate (DPPA), 1,2-Distearoyl-sn-Glycero-3-Phosphate (DSPA), 1,2-Dioleoyl-sn-Glycero-3-Phosphate (DOPA), 1-Palmitoyl-2-Oleoyl-sn-Glycero-3-Phosphate (POPA), 1,2-Dilauroyl-sn-Glycero-3-Phosphocholine (DLPC), 1,2-Ditridecanoyl-sn-Glycero-3-Phosphocholine, 1,2-Dimyristoyl-sn-Glycero-3-Phosphocholine (DMPC), 1,2-Dipentadecanoyl-sn-Glycero-3-Phosphocholine, 1,2-Dipalmitoyl-sn-Glycero-3-Phosphocholine (DPPC), 1,2-Diheptadecanoyl-sn-Glycero-3-Phosphocholine, 1,2-Distearoyl-sn-Glycero-3-Phosphocholine (DSPC), 1,2-Dimyristoleoyl-sn-Glycero-3-Phosphocholine, 1,2-

Dipalmitoleoyl-sn-Glycero-3-Phosphocholine, 1,2-Dioleoyl-sn-Glycero-3-Phosphocholine (DOPC), 1-Myristoyl-2-Palmitoyl-sn-Glycero-3-Phosphocholine, 1-Myristoyl-2-Stearoyl-sn-Glycero-3-Phosphocholine, 1-Palmitoyl-2-Myristoyl-sn-Glycero-3-Phosphocholine, 1-Palmitoyl-2-Stearoyl-sn-Glycero-3-Phosphocholine, 1-Palmitoyl-2-Oleoyl-sn-Glycero-3-Phosphocholine (POPC), 1-Palmitoyl-2-Linoleoyl-sn-Glycero-3-Phosphocholine, 1,2-Dilauroyl-sn-Glycero-3-Phosphoethanolamine (DLPE), 1,2-Dimyristoyl-sn-Glycero-3-Phosphoethanolamine (DMPE), 1,2-Dipalmitoyl-sn-Glycero-3-Phosphoethanolamine (DPPE), 1,2-Dipalmitoleoyl-sn-Glycero-3-Phosphoethanolamine, 1,2-Distearoyl-sn-Glycero-3-Phosphoethanolamine (DSPE), 1,2-Dioleoyl-sn-Glycero-3-Phosphoethanolamine (DOPE), 1-Palmitoyl-2-Oleoyl-sn-Glycero-3-Phosphoethanolamine (POPE), 1,2-Dilauroyl-sn-Glycero-3-[Phospho-RAC-(1-glycerol)] (DLPG), 1,2-Dimyristoyl-sn-Glycero-3-[Phospho-RAC-(1-glycerol)] (DMPG), 1,2-Dipalmitoyl-sn-Glycero-3-[Phospho-RAC-(1-glycerol)] (DPPG), 1,2-Distearoyl-sn-Glycero-3-[Phospho-RAC-(1-glycerol)] (DSPG), 1,2-Dioleoyl-sn-Glycero-3-[Phospho-RAC-(1-glycerol)] (DOPG), 1-Palmitoyl-2-Oleoyl-sn-Glycero-3-[Phospho-RAC-(1-glycerol)] (POPG), 1,2-Dilauroyl-sn-Glycero-3-[Phospho-L-Serine] (DLPS), 1,2-Dimyristoyl-sn-Glycero-3-[Phospho-L-Serine] (DMPS), 1,2-Dipalmitoyl-sn-Glycero-3-[Phospho-L-Serine] (DPPS), 1,2-Distearoyl-sn-Glycero-3-[Phospho-L-Serine] (DSPS), 1,2-Dioleoyl-sn-Glycero-3-[Phospho-L-Serine] (DOPS), 1-Palmitoyl-2-Oleoyl-sn-Glycero-3-[Phospho-L-Serine] (POPS).

EXAMPLE 13

This example illustrates the immunization of mice and rabbits with SPA-1-liposome formulations.

Groups of female BALB/c mice (Charles River Laboratories, St-Constant, Quebec, Canada) are immunized intramuscularly (IM) four times at two-week intervals with 20 µg of recombinant SPA-1 incorporated into different liposome preparations or, as control, with protein-free liposome formulations. Blood samples are collected from the orbital sinus prior to each immunization and two weeks after the last injection. The serum samples are stored at −20° C.

New Zealand White female rabbits (2.5 Kg, Charles River) are immunized IM three or four times at three-week intervals at several sites with 100 µg of recombinant SPA-1 protein incorporated in different liposome formulations. Serum samples are collected before each immunization and three weeks after the last injection. The serum samples are stored at −20° C.

What is claimed is:

1. An isolated polypeptide consisting of the amino acid sequence set forth as SEQ ID NO:4 from which the signal peptide sequence set forth as SEQ ID NO:38 is deleted, wherein the polypeptide is capable of eliciting an immune response in a host to *Pseudomonas aeruginosa*.

2. A pharmaceutical composition comprising a pharmaceutically acceptable carrier or diluent and an amount of a polypeptide that is capable of eliciting an immune response in a host to *Pseudomonas aeruginosa*, wherein the polypeptide consists of an amino acid sequence at least 95% identical to the amino acid sequence set forth as SEQ ID NO:4, and wherein the polypeptide is capable of inducing an antibody that binds specifically to a SPA-2 polypeptide consisting of the amino acid sequence set forth as SEQ ID NO:4.

3. A pharmaceutical composition comprising a polypeptide and a liposome, wherein the polypeptide consists of an amino acid sequence at least 95% identical to the amino acid sequence set forth as SEQ ID NO:4, and wherein the polypeptide is capable of eliciting an immune response in a host to *Pseudomonas aeruginosa*, and wherein the polypeptide is capable of inducing an antibody that binds specifically to a SPA-2 polypeptide consisting of the amino acid sequence set forth as SEQ ID NO:4.

4. The pharmaceutical composition of claim 2 wherein the polypeptide consists of the amino acid sequence set forth as SEQ ID NO:4 from which the signal peptide sequence set forth as SEQ ID NO:38 is deleted.

5. The pharmaceutical composition of claim 2 wherein the polypeptide consists of the amino acid sequence set forth as SEQ ID NO:4.

6. The pharmaceutical composition of claim 3 wherein the polypeptide consists of the amino acid sequence set forth as SEQ ID NO:4 from which the signal peptide sequence set forth as SEQ ID NO:38 has been deleted.

7. The pharmaceutical composition of claim 3 wherein the polypeptide consists of the amino acid sequence set forth as SEQ ID NO:4.

8. The pharmaceutical composition according to claim 2 further comprising a pharmaceutically acceptable adjuvant.

9. The pharmaceutical composition according to claim 3 further comprising a pharmaceutically acceptable adjuvant.

10. A kit comprising a polypeptide for detection or diagnosis of *Pseudomonas aeruginosa* infection, wherein the polypeptide consists of the amino acid sequence set forth as SEQ ID NO:4 from which the signal peptide sequence set forth as SEQ ID NO:38 is deleted.

* * * * *

```
                             SEQUENCE LISTING

<160> NUMBER OF SEQ ID NOS: 36

<210> SEQ ID NO 1
<211> LENGTH: 1347
<212> TYPE: DNA
<213> ORGANISM: Pseudomonas aeruginosa

<400> SEQUENCE: 1
atgcgtaacc ccgaacgatc cgccctgctg aaggtgagcg ggctgctggg cagcaccgtc      60
gtcgccatgg ggcttggcct ctccagcgcc tgcgcgcaga agaatccgac agtcgaatac     120
aaccagcctg ccgctcccct gcagaccaag gcgcccttct ccggcgccgg cccggccgcc     180
tcggtgcccg ctggcgcgcc gaacgaggcc cagcctgggc aaagcttcga acagtggcgc     240
gacgccttcc gtcaacaggc gctggccggt ggaatcgatg cgcagacctt cgatcgcgcc     300
ttcgccggcg tccagcccga tcccgccgtg gtcgaagcag accgcagcca gccggaattc     360
acccgaccgg tatggaagta cctggaaggc gccctcgatc cgctgcgcgt tcgccagggc     420
caggcgcgcc tggcgcagca tgcgcgcatc ctcggcgaag tcgacgcgcg ctatgcggtg     480
gatgcggatg cggtggtggc gatctgggc atggagagca actacggttc gcacatgggc     540
aacaagaacg tgatccgctc cctggcgacc ctcgcctatg aaggacgccg cccggaattc     600
gcccacgccc agttgctcgc cgccctgaag attctccagc acggcgacgt tccggcctcc     660
ttcatgatcg gctcctgggc cggcgccatg ggccagaccc agttcatccc gaccacccac     720
aaccagtatg ccgtggactt cgacggcgac ggcaagcgtg acatctgggg ctcgcccggc     780
gacgccctgg cctccaccgc caactacctg aaagcctccg gctggatcgc cggacaaccc     840
tggggtttcg aagtccgcct gccggcaggc ttcgactatt ccctggcgga actcaccatc     900
cgcaagcccc tgggcgaatg gcaagggatg ggcgtacaag gcgtcaacgg cggcccctg      960 ccctccggac tctccggcga acaggcctcg ctgctgctgc cggccgggca ccgcggcccg    1020
gccttcctgg tgctgcacaa cttccgcgcc atcctcaagt acaacaactc cagcgcctac    1080
```

-continued

```
gccctggccg tcggcctgct cgccgacagc ttcaagggcg gcggccggat agtcggcgcc    1140
tggccgctgg aggatgttcc gctgagccgc tcgcagcgca tcgagctgca acggcaactg    1200
gccgcccgcg acacgatcc gggcgcggtg gatggcatca tcggcgccaa tacgcgcaag    1260
gcgatccgcg cctgccagca ggagttcggc tggccggcgg acggctatcc gaccccggcg    1320
ctgctcgacc gcctgcggac gccatag                                        1347
```

<210> SEQ ID NO 2
<211> LENGTH: 448
<212> TYPE: PRT
<213> ORGANISM: Pseudomonas aeruginosa

<400> SEQUENCE: 2

```
Met Arg Asn Pro Glu Arg Ser Ala Leu Leu Lys Val Ser Gly Leu Leu
1               5                   10                  15

Gly Ser Thr Val Val Ala Met Gly Leu Gly Leu Ser Ser Ala Cys Ala
            20                  25                  30

Gln Lys Asn Pro Thr Val Glu Tyr Asn Gln Pro Ala Ala Pro Leu Gln
        35                  40                  45

Thr Lys Ala Pro Phe Ser Gly Ala Gly Pro Ala Ala Ser Val Pro Ala
    50                  55                  60

Gly Ala Pro Asn Glu Ala Gln Pro Gly Gln Ser Phe Glu Gln Trp Arg
65                  70                  75                  80

Asp Ala Phe Arg Gln Gln Ala Leu Ala Gly Gly Ile Asp Ala Gln Thr
                85                  90                  95

Phe Asp Arg Ala Phe Ala Gly Val Gln Pro Asp Pro Ala Val Val Glu
            100                 105                 110

Ala Asp Arg Ser Gln Pro Glu Phe Thr Arg Pro Val Trp Lys Tyr Leu
        115                 120                 125

Glu Gly Ala Leu Asp Pro Leu Arg Val Arg Gln Gly Gln Ala Arg Leu
    130                 135                 140

Ala Gln His Ala Arg Ile Leu Gly Glu Val Asp Ala Arg Tyr Ala Val
145                 150                 155                 160

Asp Ala Asp Ala Val Val Ala Ile Trp Gly Met Glu Ser Asn Tyr Gly
                165                 170                 175

Ser His Met Gly Asn Lys Asn Val Ile Arg Ser Leu Ala Thr Leu Ala
            180                 185                 190

Tyr Glu Gly Arg Arg Pro Glu Phe Ala His Ala Gln Leu Leu Ala Ala
        195                 200                 205

Leu Lys Ile Leu Gln His Gly Asp Val Pro Ala Ser Phe Met Ile Gly
    210                 215                 220

Ser Trp Ala Gly Ala Met Gly Gln Thr Gln Phe Ile Pro Thr Thr His
225                 230                 235                 240

Asn Gln Tyr Ala Val Asp Phe Asp Gly Asp Gly Lys Arg Asp Ile Trp
                245                 250                 255

Gly Ser Pro Gly Asp Ala Leu Ala Ser Thr Ala Asn Tyr Leu Lys Ala
            260                 265                 270

Ser Gly Trp Ile Ala Gly Gln Pro Trp Gly Phe Glu Val Arg Leu Pro
        275                 280                 285

Ala Gly Phe Asp Tyr Ser Leu Ala Glu Leu Thr Ile Arg Lys Pro Leu
    290                 295                 300

Gly Glu Trp Gln Gly Met Gly Val Gln Gly Val Asn Gly Gly Pro Leu
305                 310                 315                 320
```

Pro Ser Gly Leu Ser Gly Glu Gln Ala Ser Leu Leu Pro Ala Gly
            325                 330                 335

His Arg Gly Pro Ala Phe Leu Val Leu His Asn Phe Arg Ala Ile Leu
            340                 345                 350

Lys Tyr Asn Asn Ser Ser Ala Tyr Ala Leu Ala Val Gly Leu Leu Ala
            355                 360                 365

Asp Ser Phe Lys Gly Gly Gly Arg Ile Val Gly Ala Trp Pro Leu Glu
        370                 375                 380

Asp Val Pro Leu Ser Arg Ser Gln Arg Ile Glu Leu Gln Arg Gln Leu
385                 390                 395                 400

Ala Ala Arg Gly His Asp Pro Gly Ala Val Asp Gly Ile Ile Gly Ala
                405                 410                 415

Asn Thr Arg Lys Ala Ile Arg Ala Cys Gln Gln Glu Phe Gly Trp Pro
            420                 425                 430

Ala Asp Gly Tyr Pro Thr Pro Ala Leu Leu Asp Arg Leu Arg Thr Pro
            435                 440                 445

<210> SEQ ID NO 3
<211> LENGTH: 624
<212> TYPE: DNA
<213> ORGANISM: Pseudomonas aeruginosa

<400> SEQUENCE: 3
atgaaacgta tcctgaccag cgccgcgctg atcggtatga ccaccctgct ggccgcctgc      60
ggcttccaac tgcgcggcct gggcgatgcg caattcgcgc tcaaggaaat cgacgtgtcc     120
gcgcgcaacg cctacggccc gaccgtgcgc gaactgaagg aaaaccctgga aaacagcggc    180 gtgaaggtca ccagcaacgc gccctaccac ctggtgctgg tccgcgagga caaccagcag    240
cgcaccgtca gctacaccgg ttccgcgcgc ggcgcggagt tcgagctgac caacacgatc    300
aactacgaga tcgtcggcgc caacgacctg gtcctgatga gcaaccaggt acaggtgcag    360
aaggtctacg tgcacgacga aaacaacctg atcggttccg accaggaagc cgcgcagctg    420
cgcagcgaga tgcggcgcga cctgatccag cagttgtcca tgcgcctcca ggcgctgacc    480
ccggcgcaac tcgacgaagc ccagcgccag gcagaagcca aggccaaggc ggaagccgaa    540
gccctgcgcg ccgccgacga ggcggagcgc cagcgccgcg ccgccgagcc gcagcagtcg    600
ccgatcgagt tccccacccc gtga                                            624

<210> SEQ ID NO 4
<211> LENGTH: 207
<212> TYPE: PRT
<213> ORGANISM: Pseudomonas aeruginosa

<400> SEQUENCE: 4

Met Lys Arg Ile Leu Thr Ser Ala Ala Leu Ile Gly Met Thr Thr Leu
1               5                   10                  15

Leu Ala Ala Cys Gly Phe Gln Leu Arg Gly Leu Gly Asp Ala Gln Phe
            20                  25                  30

Ala Leu Lys Glu Ile Asp Val Ser Ala Arg Asn Ala Tyr Gly Pro Thr
        35                  40                  45

Val Arg Glu Leu Lys Glu Thr Leu Glu Asn Ser Gly Val Lys Val Thr
    50                  55                  60

Ser Asn Ala Pro Tyr His Leu Val Leu Val Arg Glu Asp Asn Gln Gln
65                  70                  75                  80

Arg Thr Val Ser Tyr Thr Gly Ser Ala Arg Gly Ala Glu Phe Glu Leu
                85                  90                  95

```
Thr Asn Thr Ile Asn Tyr Glu Ile Val Gly Ala Asn Asp Leu Val Leu
            100                 105                 110

Met Ser Asn Gln Val Gln Val Gln Lys Val Tyr Val His Asp Glu Asn
        115                 120                 125

Asn Leu Ile Gly Ser Asp Gln Glu Ala Ala Gln Leu Arg Ser Glu Met
    130                 135                 140

Arg Arg Asp Leu Ile Gln Gln Leu Ser Met Arg Leu Gln Ala Leu Thr
145                 150                 155                 160

Pro Ala Gln Leu Asp Glu Ala Gln Arg Gln Ala Glu Ala Lys Ala Lys
                165                 170                 175

Ala Glu Ala Glu Ala Leu Arg Ala Ala Asp Glu Ala Glu Arg Gln Arg
            180                 185                 190

Arg Ala Ala Glu Pro Gln Gln Ser Pro Ile Glu Phe Pro Thr Pro
        195                 200                 205
```

<210> SEQ ID NO 5
<211> LENGTH: 1143
<212> TYPE: DNA
<213> ORGANISM: Pseudomonas aeruginosa

<400> SEQUENCE: 5

```
atggtgcaat ggaaacacgc ggcgctgctc gccctggccc tggcggtcgt gggttgcagc     60
agcaacagca agaaggaact cccgcccgcc gaactgaccg acttcaaaga ggaagtcgtg    120
ttgagcaagc agtggagccg ctcggtcggt gatggtcagg cgacctgta caacctgctc    180
gaaccggccg tcgatggttc caccatctac gccgcgtccg ccgaagggcg ggtgatggcg    240
atccagcgcg agaccggcga cgtgctctgg aagaaggacc tggaacgtcc ggtttccggc    300
ggtgtcggcg ttggctacgg cctggtgctg gtgggtaccc tgcgcggtga cgtgatcgcc    360
ctcgacgaag ccaccggcaa gaagaagtgg accaagcgag tcaacagcga agtgctgtcg    420
gcgccggcca ccaatggcga cgtggtggtg gtgcagaccc aggacgacaa gctgatcggc    480
ctcgatgcgg ccagcggcga ccagcgctgg atctacgaaa gcaccgtgcc ggtgctgacc    540
ctgcgcggca ccggcgcgcc gctgattgcc ggcaacatgg ccctggctgg cctggccagc    600
ggcaaggtag tggcggtcga cgtacagcgc ggcctgccga tctgggagca gcggtagcg    660
attccccagg ggcgttccga actggatcgc gtggtggaca tcgacggcgg cctcctgctg    720
tccggcgaca ccctctacgt ggtcagctac cagggccgtg ccgcggcgct ggacgtgaac    780
agcggccgcc tgctctggca gcgcgaagcg tcgagctacg tcggcgtcgc cgaaggcttc    840
ggcaatatct acgtcagcca ggccagcggt tcggtggaag gcctggactc gcgcggcgct    900
tcttcgctgt ggaacaacga cgccctggcg cgtcgccaac tgtcggctcc ggcggtgttc    960
tccagcaacg tggtggtcgg cgacctggaa ggctacgtgc acctgctgag ccaggtggac   1020
ggtcgcttcg tcggtcgcga gcgggtcgac agcgatggcg tgcgggttcg tccgctggtg   1080
gtcgggagct ggatgtacgt gttcggcaac ggtggcaagc tcgtcgccta ccatccgc    1140
tag                                                                1143
```

<210> SEQ ID NO 6
<211> LENGTH: 380
<212> TYPE: PRT
<213> ORGANISM: Pseudomonas aeruginosa

<400> SEQUENCE: 6

Met Val Gln Trp Lys His Ala Ala Leu Leu Ala Leu Ala Leu Ala Val

```
                1               5                  10                 15
Val Gly Cys Ser Ser Asn Ser Lys Lys Glu Leu Pro Pro Ala Glu Leu
                    20                  25                 30

Thr Asp Phe Lys Glu Val Val Leu Ser Lys Gln Trp Ser Arg Ser
            35                  40                  45

Val Gly Asp Gly Gln Gly Asp Leu Tyr Asn Leu Leu Glu Pro Ala Val
        50                  55                  60

Asp Gly Ser Thr Ile Tyr Ala Ala Ser Ala Glu Gly Arg Val Met Ala
65                      70                  75                      80

Ile Gln Arg Glu Thr Gly Asp Val Leu Trp Lys Lys Asp Leu Glu Arg
                85                  90                  95

Pro Val Ser Gly Gly Val Gly Val Gly Tyr Gly Leu Val Leu Val Gly
                    100                 105                110

Thr Leu Arg Gly Asp Val Ile Ala Leu Asp Glu Ala Thr Gly Lys Lys
            115                 120                 125

Lys Trp Thr Lys Arg Val Asn Ser Glu Val Leu Ser Ala Pro Ala Thr
        130                 135                 140

Asn Gly Asp Val Val Val Gln Thr Gln Asp Asp Lys Leu Ile Gly
145                     150                 155                 160

Leu Asp Ala Ala Ser Gly Asp Gln Arg Trp Ile Tyr Glu Ser Thr Val
                165                 170                 175

Pro Val Leu Thr Leu Arg Gly Thr Gly Ala Pro Leu Ile Ala Gly Asn
                    180                 185                 190

Met Ala Leu Ala Gly Leu Ala Ser Gly Lys Val Val Ala Val Asp Val
            195                 200                 205

Gln Arg Gly Leu Pro Ile Trp Glu Gln Arg Val Ala Ile Pro Gln Gly
        210                 215                 220

Arg Ser Glu Leu Asp Arg Val Val Asp Ile Asp Gly Gly Leu Leu Leu
225                     230                 235                 240

Ser Gly Asp Thr Leu Tyr Val Val Ser Tyr Gln Gly Arg Ala Ala Ala
                245                 250                 255

Leu Asp Val Asn Ser Gly Arg Leu Leu Trp Gln Arg Glu Ala Ser Ser
                    260                 265                 270

Tyr Val Gly Val Ala Glu Gly Phe Gly Asn Ile Tyr Val Ser Gln Ala
            275                 280                 285

Ser Gly Ser Val Glu Gly Leu Asp Ser Arg Gly Ala Ser Ser Leu Trp
        290                 295                 300

Asn Asn Asp Ala Leu Ala Arg Arg Gln Leu Ser Ala Pro Ala Val Phe
305                     310                 315                 320

Ser Ser Asn Val Val Gly Asp Leu Glu Gly Tyr Val His Leu Leu
                325                 330                 335

Ser Gln Val Asp Gly Arg Phe Val Gly Arg Glu Arg Val Asp Ser Asp
            340                 345                 350

Gly Val Arg Val Arg Pro Leu Val Gly Ser Trp Met Tyr Val Phe
        355                 360                 365

Gly Asn Gly Gly Lys Leu Val Ala Tyr Thr Ile Arg
370                     375                 380
```

<210> SEQ ID NO 7
<211> LENGTH: 36
<212> TYPE: DNA
<213> ORGANISM: Artificial Sequence
<220> FEATURE:
<223> OTHER INFORMATION: primer sequence

```
<400> SEQUENCE: 7
gggaattcca tatggcgcag aagaatccga cagtcg                                36

<210> SEQ ID NO 8
<211> LENGTH: 33
<212> TYPE: DNA
<213> ORGANISM: Artificial Sequence
<220> FEATURE:
<223> OTHER INFORMATION: primer sequence

<400> SEQUENCE: 8
ataagaatgc ggccgctggc gtccgcaggc ggt                                   33

<210> SEQ ID NO 9
<211> LENGTH: 30
<212> TYPE: DNA
<213> ORGANISM: Artificial Sequence
<220> FEATURE:
<223> OTHER INFORMATION: primer sequence

<400> SEQUENCE: 9
gggcagatct tgatggcgca gaagaatccg                                      30

<210> SEQ ID NO 10
<211> LENGTH: 30
<212> TYPE: DNA
<213> ORGANISM: Artificial Sequence
<220> FEATURE:
<223> OTHER INFORMATION: primer sequence

<400> SEQUENCE: 10
gatcctctag attggcgtcc gcaggcggtc                                      30

<210> SEQ ID NO 11
<211> LENGTH: 31
<212> TYPE: DNA
<213> ORGANISM: Artificial Sequence
<220> FEATURE:
<223> OTHER INFORMATION: primer sequence

<400> SEQUENCE: 11
gggaattcca tatgggcttc caactgcgcg g                                    31

<210> SEQ ID NO 12
<211> LENGTH: 28
<212> TYPE: DNA
<213> ORGANISM: Artificial Sequence
<220> FEATURE:
<223> OTHER INFORMATION: primer sequence

<400> SEQUENCE: 12
cgccaagctt cggggtgggg aactcgat                                        28

<210> SEQ ID NO 13
<211> LENGTH: 30
<212> TYPE: DNA
<213> ORGANISM: Artificial Sequence
<220> FEATURE:
<223> OTHER INFORMATION: primer sequence

<400> SEQUENCE: 13
cgaggatcct atgtgcggct tccaactgcg                                      30

<210> SEQ ID NO 14
<211> LENGTH: 31
```

<212> TYPE: DNA
<213> ORGANISM: Artificial Sequence
<220> FEATURE:
<223> OTHER INFORMATION: primer sequence

<400> SEQUENCE: 14
cagaagcttc ggggtgggga actcgatcgg c                                    31

<210> SEQ ID NO 15
<211> LENGTH: 38
<212> TYPE: DNA
<213> ORGANISM: Artificial Sequence
<220> FEATURE:
<223> OTHER INFORMATION: primer sequence

<400> SEQUENCE: 15
gggaattcca tatgagcagc aacagcaaga aggaactc                             38

<210> SEQ ID NO 16
<211> LENGTH: 28
<212> TYPE: DNA
<213> ORGANISM: Artificial Sequence
<220> FEATURE:
<223> OTHER INFORMATION: primer sequence

<400> SEQUENCE: 16
cgccaagctt gcggatggtg taggcgac                                        28

<210> SEQ ID NO 17
<211> LENGTH: 30
<212> TYPE: DNA
<213> ORGANISM: Artificial Sequence
<220> FEATURE:
<223> OTHER INFORMATION: primer sequence

<400> SEQUENCE: 17
cgaggatcct atgagcaaga aggaactccc                                      30

<210> SEQ ID NO 18
<211> LENGTH: 31
<212> TYPE: DNA
<213> ORGANISM: Artificial Sequence
<220> FEATURE:
<223> OTHER INFORMATION: primer sequence

<400> SEQUENCE: 18
cagaagcttc tagcggattg gtgtaggcga c                                    31

<210> SEQ ID NO 19
<211> LENGTH: 1197
<212> TYPE: DNA
<213> ORGANISM: Pseudomonas aeruginosa

<400> SEQUENCE: 19
atgcgcagcc ttcttctctc ctcgctggcc ctgctacccg ccctggccct ggcgcaaccc       60
gacgcctcga gcttcccttc ctgcctgccg ggcctgcaga agaaggccca ggcgcagggc      120
atttccgccg acagttatga gcgcttcacc agcggcctgc aggccgacct cagcgtgctc      180
gacctgctcg acgcgcagcc ggagttcacc accccgctgt gggactacct ggccggcctg      240
gtggacgagc agcgggtcag cgatggcaag gcgatgctcg cccagcacga caagctgctc      300
gaccaggtgg ccgcgcgcta cggcgtggac aagtacacgg tggtggcggt gtggggcgtg      360
gaaagcgact acgggcggat cttcggcaag cgtccgctgc tgacctcgct gtcgaccctg      420

-continued

```
tcctgctacg ggcgccgcca gtcgttcttc cagggcgagt tcctcgccac cctgaagctg    480
ttgcaggccg gcgacatccg cgacgccggc atcaccggct cctgggccgg ggccttcggc    540 cataccagt  tcatgccatc gacctacgcg cggatcgccg tggacttcga cggcgacggt    600
cgccgcgacc tggtaggcag cgtgccggat gccctcggtt ccaccgccaa ctacctgaag    660
aaggctggct ggcgcacggg acagccgtgg ggctatgaag tgaaggtgcc ggccgacttc    720
cccgccagcc tggccgggcg cggcaagcgc cagccgctgt cggcctgggt cgcccgtggg    780
gtgaggcggg tcgacggcca gccgctgccg ggcggcgacg agaaggccgc gatcctcctg    840
ccggccgggg cccagggccc ggccttcctg gtctatcgca actacgatgc gatctattcc    900
tacaacgccg cggaaagcta cgcgctggcc atcgccctgc tttccgaccg cctgcgcggc    960
ggcagcggcc tggtggcgtc ctggccgacc gacgacccgg gcatcagccg gctcgagcgc   1020
aagcaattgc agaaggcgtt gctggcgcgc ggctacgaca tcggcgaggc cgacgggctg   1080
atcggcacca gcacgcgcaa ggcgatccag gccgagcaga gcgcctcgg  cctgaccccg   1140 gccgacggtc gcgccgggcg caagatcctc gaggcgctga agggcgccca gccctga      1197
```

<210> SEQ ID NO 20
<211> LENGTH: 398
<212> TYPE: PRT
<213> ORGANISM: Pseudomonas aeruginosa

<400> SEQUENCE: 20

```
Met Arg Ser Leu Leu Ser Ser Leu Ala Leu Leu Pro Ala Leu Ala
1               5                  10                  15

Leu Ala Gln Pro Asp Ala Ser Ser Phe Pro Ser Cys Leu Ala Gly Leu
            20                  25                  30

Gln Lys Lys Ala Gln Ala Gln Gly Ile Ser Ala Asp Ser Tyr Glu Arg
        35                  40                  45

Phe Thr Ser Gly Leu Gln Ala Asp Leu Ser Val Leu Asp Leu Leu Asp
    50                  55                  60

Ala Gln Pro Glu Phe Thr Thr Pro Leu Trp Asp Tyr Leu Ala Gly Leu
65                  70                  75                  80

Val Asp Glu Gln Arg Val Ser Asp Gly Lys Ala Met Leu Ala Gln His
                85                  90                  95

Asp Lys Leu Leu Asp Gln Val Ala Ala Arg Tyr Gly Val Asp Lys Tyr
            100                 105                 110

Thr Val Val Ala Val Trp Gly Val Glu Ser Asp Tyr Gly Arg Ile Phe
        115                 120                 125

Gly Lys Arg Pro Leu Leu Thr Ser Leu Ser Thr Leu Ser Cys Tyr Gly
    130                 135                 140

Arg Arg Gln Ser Phe Phe Gln Gly Glu Phe Leu Ala Thr Leu Lys Leu
145                 150                 155                 160

Leu Gln Ala Gly Asp Ile Arg Asp Ala Gly Ile Thr Gly Ser Trp Ala
                165                 170                 175

Gly Ala Phe Gly His Thr Gln Phe Met Pro Ser Thr Tyr Ala Arg Ile
            180                 185                 190

Ala Val Asp Phe Asp Gly Asp Gly Arg Arg Asp Leu Val Gly Ser Val
        195                 200                 205

Pro Asp Ala Leu Gly Ser Thr Ala Asn Tyr Leu Lys Lys Ala Gly Trp
    210                 215                 220

Arg Thr Gly Gln Pro Trp Gly Tyr Glu Val Lys Val Pro Ala Asp Phe
225                 230                 235                 240
```

-continued

Pro Ala Ser Leu Ala Gly Arg Gly Lys Arg Gln Pro Leu Ser Ala Trp
                245                 250                 255

Val Ala Arg Gly Val Arg Val Asp Gly Gln Pro Leu Pro Gly Gly
            260                 265                 270

Asp Glu Lys Ala Ala Ile Leu Leu Pro Ala Gly Ala Gln Gly Pro Ala
                275                 280                 285

Phe Leu Val Tyr Arg Asn Tyr Asp Ala Ile Tyr Ser Tyr Asn Ala Ala
            290                 295                 300

Glu Ser Tyr Ala Leu Ala Ile Ala Leu Leu Ser Asp Arg Leu Arg Gly
305                 310                 315                 320

Gly Ser Gly Leu Val Ala Ser Trp Pro Thr Asp Pro Gly Ile Ser
                325                 330                 335

Arg Leu Glu Arg Lys Gln Leu Gln Lys Ala Leu Leu Ala Arg Gly Tyr
            340                 345                 350

Asp Ile Gly Glu Ala Asp Gly Leu Ile Gly Thr Ser Thr Arg Lys Ala
            355                 360                 365

Ile Gln Ala Glu Gln Lys Arg Leu Gly Leu Thr Pro Ala Asp Gly Arg
        370                 375                 380

Ala Gly Arg Lys Ile Leu Glu Ala Leu Lys Gly Ala Gln Pro
385                 390                 395

<210> SEQ ID NO 21
<211> LENGTH: 1023
<212> TYPE: DNA
<213> ORGANISM: Pseudomonas aeruginosa

<400> SEQUENCE: 21
gtgaagaacg caatgcaagt actgcgtaca tgggcggcca ggggcgtcca atgggtcggc      60
gtagccggcg tcattggcct gtccggggcg gcccaggcgg gggactacga cggctcgccg     120
caagtggccg agttcgtcag cgaaatgacc cgcgactacg gcttcgccgg agagcagctg     180
atggggctgt ccgcgacgt gaaccgcaag cagtcgatcc tcgatgcgat ctcgcgcccg     240
gccgagcggg tcaagcagtg gaaggaatac cggccgatct tcatcagcga cgcgcgcatc     300
agtcgtggcg tcgacttctg gaacaagcat gccgaagacc tggcgcgggc ggagaaggaa     360
tacggcgtgc cggccgagat catcgtctcg atcatcggcg tggaaacctt cttcggccgc     420
aacaccggca gttaccgggt gatggacgcg ctgtccaccc tcggcttcga ctacccgccg     480
cgggccgact tcttccgcaa ggagttgcgc gagttcctcc tgctcgcccg cgaacagcag     540
gtcgacccgc tcagcctgac cggctcctac gccggcgcca tgggcctgcc acaattcatg     600
ccgagcagct ccgcgcccta cgcggtggac ttcgacggcg atggccacat caatatctgg     660
agcgacccga ccgatgccat cggtagcgtc gccagctact tcaagcagca cggctgggtc     720
accggcgagc cggtggtctc ggtggccgag atcaacgacg agagcgccga gagcgcggtg     780
accaggggcg tcgacccgac catgagcctg ggcgagctgc gtgcccgcgg ctggcgcacc     840
cacgatgcgc tgcgcgacga ccagaaggtc acggcgatgc gtttcgtcgg cgacaagggc     900
atcgagtatt gggtcggttt gccgaacttc tacgtgatca cccgctataa tcgcagcgcc     960
atgtatgcca tggcggttta tcagctggcg ggcgagattg cccgcgcgcg aggtgcccat    1020
tga                                                                  1023

<210> SEQ ID NO 22
<211> LENGTH: 340
<212> TYPE: PRT
<213> ORGANISM: Pseudomonas aeruginosa

<400> SEQUENCE: 22

```
Met Lys Asn Ala Met Gln Val Leu Arg Thr Trp Ala Ala Arg Gly Val
1               5                   10                  15
Gln Trp Val Gly Val Ala Gly Val Ile Gly Leu Ser Gly Ala Ala Gln
            20                  25                  30
Ala Gly Asp Tyr Asp Gly Ser Pro Gln Val Ala Glu Phe Val Ser Glu
        35                  40                  45
Met Thr Arg Asp Tyr Gly Phe Ala Gly Glu Gln Leu Met Gly Leu Phe
    50                  55                  60
Arg Asp Val Asn Arg Lys Gln Ser Ile Leu Asp Ala Ile Ser Arg Pro
65                  70                  75                  80
Ala Glu Arg Val Lys Gln Trp Lys Glu Tyr Arg Pro Ile Phe Ile Ser
                85                  90                  95
Asp Ala Arg Ile Ser Arg Gly Val Asp Phe Trp Asn Lys His Ala Glu
            100                 105                 110
Asp Leu Ala Arg Ala Glu Lys Glu Tyr Gly Val Pro Ala Glu Ile Ile
        115                 120                 125
Val Ser Ile Ile Gly Val Glu Thr Phe Phe Gly Arg Asn Thr Gly Ser
    130                 135                 140
Tyr Arg Val Met Asp Ala Leu Ser Thr Leu Gly Phe Asp Tyr Pro Pro
145                 150                 155                 160
Arg Ala Asp Phe Phe Arg Lys Glu Leu Arg Glu Phe Leu Leu Leu Ala
                165                 170                 175
Arg Glu Gln Gln Val Asp Pro Leu Ser Leu Thr Gly Ser Tyr Ala Gly
            180                 185                 190
Ala Met Gly Leu Pro Gln Phe Met Pro Ser Ser Phe Arg Ala Tyr Ala
        195                 200                 205
Val Asp Phe Asp Gly Asp Gly His Ile Asn Ile Trp Ser Asp Pro Thr
    210                 215                 220
Asp Ala Ile Gly Ser Val Ala Ser Tyr Phe Lys Gln His Gly Trp Val
225                 230                 235                 240
Thr Gly Glu Pro Val Val Ser Val Ala Glu Ile Asn Asp Glu Ser Ala
                245                 250                 255
Glu Ser Ala Val Thr Arg Gly Val Asp Pro Thr Met Ser Leu Gly Glu
            260                 265                 270
Leu Arg Ala Arg Gly Trp Arg Thr His Asp Ala Leu Arg Asp Asp Gln
        275                 280                 285
Lys Val Thr Ala Met Arg Phe Val Gly Asp Lys Gly Ile Glu Tyr Trp
    290                 295                 300
Val Gly Leu Pro Asn Phe Tyr Val Ile Thr Arg Tyr Asn Arg Ser Ala
305                 310                 315                 320
Met Tyr Ala Met Ala Val Tyr Gln Leu Ala Gly Glu Ile Ala Arg Ala
                325                 330                 335
Arg Gly Ala His
            340
```

<210> SEQ ID NO 23
<211> LENGTH: 1104
<212> TYPE: DNA
<213> ORGANISM: Pseudomonas aeruginosa

<400> SEQUENCE: 23

```
atgcgccgta ccgccctcgc cctgcccctg ttccttctgg tctcagcatg cagcagcgaa    60
```

-continued

```
ccgacgccac caccgaaacc cgccgccaaa ccccaggccc gcaccgtcat tcaccccgc        120
cccgtacgcc agtcggtgca accgatactg ccgctgcgcg gcgattacgc gaacaatccg        180
gcggcacagc acttcatcga caggatggtc agccagcacg gcttcaaccg ccagcaactg        240
cacgatctgt tcgcccagac ccagcgcctg gactgggtga tccgcctgat ggaccggcaa        300
gccccgacct ataccccacc cagcggaccg aacggcgcct ggctgcgcta ccggaagaag        360
ttcgtcacgc caggcaacgt acagaacggc gtgctgttct gggaccaata cgaaaccgac        420
ctgcaacggg catcgcgcgt ctacggcgtg ccgccggaga tcatcgtcgg catcatcggc        480
gtggaaaccc gctgggggcg tgtgatgggc aagacgcgca tcatcgatgc gctgtccacc        540
ctgtccttct cctaccctcg ccgcgcggaa ttcttcagcg gcgaactgga gcaattcctc        600
ctccaggcgc gcaaggaagg caccgacccg ctggccctgc gcggttccta tgccggcgcc        660
atgggctacg gccagttcat gccgtcttca ttcaccaagt acgcggtgga cttcgatggc        720
gatgggcata tcgacctgtg gaatccgcgt gacgccatcg gcagcgtcgc caactatttc        780
aagcagcacg gctgggtcag cggcgatcgc gtggcggttc ccgccagtgg ccgggctccc        840
tcgctggaag atggcttcaa gacgctgtac ccgctggacg tgctcgcttc cgccggatta        900
cgcccgcagg gtccgctcgg cggccaccgg caagccagcc tgctgcgcct ggacatgggc        960
aggaactacc agtactggta cggcctgccg aacttctacg tgatcacccg ctataaccac       1020
agcacccact acgcgatggc cgtctgggaa ctgggcaagg aagtcgaccg ggtgcgtcac       1080
cgctccgtcg tcaggcagga ttag                                              1104
```

<210> SEQ ID NO 24
<211> LENGTH: 367
<212> TYPE: PRT
<213> ORGANISM: Pseudomonas aeruginosa

<400> SEQUENCE: 24

```
Met Arg Arg Thr Ala Leu Ala Leu Pro Leu Phe Leu Leu Val Ser Ala
1               5                   10                  15

Cys Ser Ser Glu Pro Thr Pro Pro Lys Pro Ala Ala Lys Pro Gln
            20                  25                  30

Ala Arg Thr Val Ile Ser Pro Arg Pro Val Arg Gln Ser Val Gln Pro
        35                  40                  45

Ile Leu Pro Leu Arg Gly Asp Tyr Ala Asn Asn Pro Ala Ala Gln His
    50                  55                  60

Phe Ile Asp Arg Met Val Ser Gln His Gly Phe Asn Arg Gln Gln Leu
65                  70                  75                  80

His Asp Leu Phe Ala Gln Thr Gln Arg Leu Asp Trp Val Ile Arg Leu
                85                  90                  95

Met Asp Arg Gln Ala Pro Thr Tyr Thr Pro Pro Ser Gly Pro Asn Gly
            100                 105                 110

Ala Trp Leu Arg Tyr Arg Lys Lys Phe Val Thr Pro Gly Asn Val Gln
        115                 120                 125

Asn Gly Val Leu Phe Trp Asp Gln Tyr Glu Thr Asp Leu Gln Arg Ala
    130                 135                 140

Ser Arg Val Tyr Gly Val Pro Pro Glu Ile Ile Val Gly Ile Ile Gly
145                 150                 155                 160

Val Glu Thr Arg Trp Gly Arg Val Met Gly Lys Thr Arg Ile Ile Asp
                165                 170                 175

Ala Leu Ser Thr Leu Ser Phe Ser Tyr Pro Arg Arg Ala Glu Phe Phe
            180                 185                 190
```

```
Ser Gly Glu Leu Glu Gln Phe Leu Leu Gln Ala Arg Lys Glu Gly Thr
        195                 200                 205

Asp Pro Leu Ala Leu Arg Gly Ser Tyr Ala Gly Ala Met Gly Tyr Gly
    210                 215                 220

Gln Phe Met Pro Ser Ser Phe Thr Lys Tyr Ala Val Asp Phe Asp Gly
225                 230                 235                 240

Asp Gly His Ile Asp Leu Trp Asn Pro Arg Asp Ala Ile Gly Ser Val
                245                 250                 255

Ala Asn Tyr Phe Lys Gln His Gly Trp Val Ser Gly Asp Arg Val Ala
            260                 265                 270

Val Pro Ala Ser Gly Arg Ala Pro Ser Leu Glu Asp Gly Phe Lys Thr
        275                 280                 285

Leu Tyr Pro Leu Asp Val Leu Ala Ser Ala Gly Leu Arg Pro Gln Gly
    290                 295                 300

Pro Leu Gly Gly His Arg Gln Ala Ser Leu Leu Arg Leu Asp Met Gly
305                 310                 315                 320

Arg Asn Tyr Gln Tyr Trp Tyr Gly Leu Pro Asn Phe Tyr Val Ile Thr
                325                 330                 335

Arg Tyr Asn His Ser Thr His Tyr Ala Met Ala Val Trp Glu Leu Gly
            340                 345                 350

Lys Glu Val Asp Arg Val Arg His Arg Ser Val Val Arg Gln Asp
        355                 360                 365

<210> SEQ ID NO 25
<211> LENGTH: 42
<212> TYPE: DNA
<213> ORGANISM: Artificial Sequence
<220> FEATURE:
<223> OTHER INFORMATION: primer sequence

<400> SEQUENCE: 25
gagttccata tgagcttccc ttcctgcctc gccggcctgc ag                      42

<210> SEQ ID NO 26
<211> LENGTH: 41
<212> TYPE: DNA
<213> ORGANISM: Artificial Sequence
<220> FEATURE:
<223> OTHER INFORMATION: primer sequence

<400> SEQUENCE: 26
cgctgaggat cctcacttct gcaattgctt gcgctcgagc c                       41

<210> SEQ ID NO 27
<211> LENGTH: 32
<212> TYPE: DNA
<213> ORGANISM: Artificial Sequence
<220> FEATURE:
<223> OTHER INFORMATION: primer sequence

<400> SEQUENCE: 27
gggaattcca tatggggggcg gcccaggcgg cg                                32

<210> SEQ ID NO 28
<211> LENGTH: 30
<212> TYPE: DNA
<213> ORGANISM: Artificial Sequence
<220> FEATURE:
<223> OTHER INFORMATION: primer sequence

<400> SEQUENCE: 28
```

```
gcgctgagga tcctcaatgg gcacctcgcg                                    30
```

<210> SEQ ID NO 29
<211> LENGTH: 30
<212> TYPE: DNA
<213> ORGANISM: Artificial Sequence
<220> FEATURE:
<223> OTHER INFORMATION: primer sequence

<400> SEQUENCE: 29

```
gggaattcca tatgagcagc gaaccgacgc                                    30
```

<210> SEQ ID NO 30
<211> LENGTH: 30
<212> TYPE: DNA
<213> ORGANISM: Artificial Sequence
<220> FEATURE:
<223> OTHER INFORMATION: primer sequence

<400> SEQUENCE: 30

```
cgccaagctt ctaatcctgc ctgacgacgg                                    30
```

<210> SEQ ID NO 31
<211> LENGTH: 419
<212> TYPE: PRT
<213> ORGANISM: Pseudomonas aeruginosa

<400> SEQUENCE: 31

```
Ala Cys Ala Gln Lys Asn Pro Thr Val Glu Tyr Asn Gln Pro Ala Ala
 1               5                  10                  15

Pro Leu Gln Thr Lys Ala Pro Phe Ser Gly Ala Gly Pro Ala Ala Ser
                20                  25                  30

Val Pro Ala Gly Ala Pro Asn Glu Ala Gln Pro Gly Gln Ser Phe Glu
            35                  40                  45

Gln Trp Arg Asp Ala Phe Arg Gln Ala Leu Ala Gly Gly Ile Asp
        50                  55                  60

Ala Gln Thr Phe Asp Arg Ala Phe Ala Gly Val Gln Pro Asp Pro Ala
 65                  70                  75                  80

Val Val Glu Ala Asp Arg Ser Gln Pro Glu Phe Thr Arg Pro Val Trp
                 85                  90                  95

Lys Tyr Leu Glu Gly Ala Leu Asp Pro Leu Arg Val Arg Gln Gly Gln
            100                 105                 110

Ala Arg Leu Ala Gln His Ala Arg Ile Leu Gly Glu Val Asp Ala Arg
        115                 120                 125

Tyr Ala Val Asp Ala Asp Ala Val Val Ala Ile Trp Gly Met Glu Ser
    130                 135                 140

Asn Tyr Gly Ser His Met Gly Asn Lys Asn Val Ile Arg Ser Leu Ala
145                 150                 155                 160

Thr Leu Ala Tyr Glu Gly Arg Arg Pro Glu Phe Ala His Ala Gln Leu
                165                 170                 175

Leu Ala Ala Leu Lys Ile Leu Gln His Gly Asp Val Pro Ala Ser Phe
            180                 185                 190

Met Ile Gly Ser Trp Ala Gly Ala Met Gly Gln Thr Gln Phe Ile Pro
        195                 200                 205

Thr Thr His Asn Gln Tyr Ala Val Asp Phe Asp Gly Asp Gly Lys Arg
    210                 215                 220

Asp Ile Trp Gly Ser Pro Gly Asp Ala Leu Ala Ser Thr Ala Asn Tyr
225                 230                 235                 240
```

```
Leu Lys Ala Ser Gly Trp Ile Ala Gly Gln Pro Trp Gly Phe Glu Val
                245                 250                 255

Arg Leu Pro Ala Gly Phe Asp Tyr Ser Leu Ala Glu Leu Thr Ile Arg
            260                 265                 270

Lys Pro Leu Gly Glu Trp Gln Gly Met Gly Val Gln Gly Val Asn Gly
        275                 280                 285

Gly Pro Leu Pro Ser Gly Leu Ser Gly Glu Gln Ala Ser Leu Leu Leu
    290                 295                 300

Pro Ala Gly His Arg Gly Pro Ala Phe Leu Val Leu His Asn Phe Arg
305                 310                 315                 320

Ala Ile Leu Lys Tyr Asn Asn Ser Ser Ala Tyr Ala Leu Ala Val Gly
                325                 330                 335

Leu Leu Ala Asp Ser Phe Lys Gly Gly Arg Ile Val Gly Ala Trp
            340                 345                 350

Pro Leu Glu Asp Val Pro Leu Ser Arg Ser Gln Arg Ile Glu Leu Gln
        355                 360                 365

Arg Gln Leu Ala Ala Arg Gly His Asp Pro Gly Ala Val Asp Gly Ile
    370                 375                 380

Ile Gly Ala Asn Thr Arg Lys Ala Ile Arg Ala Cys Gln Gln Glu Phe
385                 390                 395                 400

Gly Trp Pro Ala Asp Gly Tyr Pro Thr Pro Ala Leu Leu Asp Arg Leu
                405                 410                 415

Arg Thr Pro

<210> SEQ ID NO 32
<211> LENGTH: 398
<212> TYPE: PRT
<213> ORGANISM: Pseudomonas aeruginosa

<400> SEQUENCE: 32

Met Arg Ser Leu Leu Ser Ser Leu Ala Leu Leu Pro Ala Leu Ala
1               5                   10                  15

Leu Ala Gln Pro Asp Ala Ser Ser Phe Pro Ser Cys Leu Ala Gly Leu
            20                  25                  30

Gln Lys Lys Ala Gln Ala Gln Gly Ile Ser Ala Asp Ser Tyr Glu Arg
        35                  40                  45

Phe Thr Ser Gly Leu Gln Ala Asp Leu Ser Val Leu Asp Leu Leu Asp
    50                  55                  60

Ala Gln Pro Glu Phe Thr Thr Pro Leu Trp Asp Tyr Leu Ala Gly Leu
65                  70                  75                  80

Val Asp Glu Gln Arg Val Ser Asp Gly Lys Ala Met Leu Ala Gln His
                85                  90                  95

Asp Lys Leu Leu Asp Gln Val Ala Ala Arg Tyr Gly Val Asp Lys Tyr
            100                 105                 110

Thr Val Val Ala Val Trp Gly Val Glu Ser Asp Tyr Gly Arg Ile Phe
        115                 120                 125

Gly Lys Arg Pro Leu Leu Thr Ser Leu Ser Thr Leu Ser Cys Tyr Gly
    130                 135                 140

Arg Arg Gln Ser Phe Phe Gln Gly Glu Phe Leu Ala Thr Leu Lys Leu
145                 150                 155                 160

Leu Gln Ala Gly Asp Ile Arg Asp Ala Gly Ile Thr Gly Ser Trp Ala
                165                 170                 175

Gly Ala Phe Gly His Thr Gln Phe Met Pro Ser Thr Tyr Ala Arg Ile
            180                 185                 190
```

```
Ala Val Asp Phe Asp Gly Asp Gly Arg Arg Asp Leu Val Gly Ser Val
            195                 200                 205

Pro Asp Ala Leu Gly Ser Thr Ala Asn Tyr Leu Lys Lys Ala Gly Trp
        210                 215                 220

Arg Thr Gly Gln Pro Trp Gly Tyr Glu Val Lys Val Pro Ala Asp Phe
225                 230                 235                 240

Pro Ala Ser Leu Ala Gly Arg Gly Lys Arg Gln Pro Leu Ser Ala Trp
                245                 250                 255

Val Ala Arg Gly Val Arg Val Asp Gly Gln Pro Leu Pro Gly Gly
            260                 265                 270

Asp Glu Lys Ala Ala Ile Leu Leu Pro Ala Gly Ala Gln Gly Pro Ala
            275                 280                 285

Phe Leu Val Tyr Arg Asn Tyr Asp Ala Ile Tyr Ser Tyr Asn Ala Ala
        290                 295                 300

Glu Ser Tyr Ala Leu Ala Ile Ala Leu Leu Ser Asp Arg Leu Arg Gly
305                 310                 315                 320

Gly Ser Gly Leu Val Ala Ser Trp Pro Thr Asp Asp Pro Gly Ile Ser
                325                 330                 335

Arg Leu Glu Arg Lys Gln Leu Gln Lys Ala Leu Leu Ala Arg Gly Tyr
            340                 345                 350

Asp Ile Gly Glu Ala Asp Gly Leu Ile Gly Thr Ser Thr Arg Lys Ala
        355                 360                 365

Ile Gln Ala Glu Gln Lys Arg Leu Gly Leu Thr Pro Ala Asp Gly Arg
370                 375                 380

Ala Gly Arg Lys Ile Leu Glu Ala Leu Lys Gly Ala Gln Pro
385                 390                 395

<210> SEQ ID NO 33
<211> LENGTH: 348
<212> TYPE: PRT
<213> ORGANISM: Pseudomonas aeruginosa

<400> SEQUENCE: 33

Val Pro Ala Gly Ala Pro Asn Glu Ala Gln Pro Gly Gln Ser Phe Glu
1               5                   10                  15

Gln Trp Arg Asp Ala Phe Arg Gln Ala Leu Ala Gly Gly Ile Asp
            20                  25                  30

Ala Gln Thr Phe Asp Arg Ala Phe Ala Gly Val Gln Pro Asp Pro Ala
        35                  40                  45

Val Val Glu Ala Asp Arg Ser Gln Pro Glu Phe Thr Arg Pro Val Trp
    50                  55                  60

Lys Tyr Leu Glu Gly Ala Leu Asp Pro Leu Arg Val Arg Gln Gly Gln
65                  70                  75                  80

Ala Arg Leu Ala Gln His Ala Arg Ile Leu Gly Glu Val Asp Ala Arg
                85                  90                  95

Tyr Ala Val Asp Ala Asp Ala Val Val Ala Ile Trp Gly Met Glu Ser
            100                 105                 110

Asn Tyr Gly Ser His Met Gly Asn Lys Asn Val Ile Arg Ser Leu Ala
        115                 120                 125

Thr Leu Ala Tyr Glu Gly Arg Arg Pro Glu Phe Ala His Ala Gln Leu
    130                 135                 140

Leu Ala Ala Leu Lys Ile Leu Gln His Gly Asp Val Pro Ala Ser Phe
145                 150                 155                 160

Met Ile Gly Ser Trp Ala Gly Ala Met Gly Gln Thr Gln Phe Ile Pro
```

```
                165                 170                 175
Thr Thr His Asn Gln Tyr Ala Val Asp Phe Asp Gly Asp Gly Lys Arg
            180                 185                 190

Asp Ile Trp Gly Ser Pro Gly Asp Ala Leu Ala Ser Thr Ala Asn Tyr
        195                 200                 205

Leu Lys Ala Ser Gly Trp Ile Ala Gly Gln Pro Trp Gly Phe Glu Val
    210                 215                 220

Arg Leu Pro Ala Gly Phe Asp Tyr Ser Leu Ala Glu Leu Thr Ile Arg
225                 230                 235                 240

Lys Pro Leu Gly Glu Trp Gln Gly Met Gly Val Gln Gly Val Asn Gly
                245                 250                 255

Gly Pro Leu Pro Ser Gly Leu Ser Gly Glu Gln Ala Ser Leu Leu Leu
            260                 265                 270

Pro Ala Gly His Arg Gly Pro Ala Phe Leu Val Leu His Asn Phe Arg
        275                 280                 285

Ala Ile Leu Lys Tyr Asn Asn Ser Ser Ala Tyr Ala Leu Ala Val Gly
    290                 295                 300

Leu Leu Ala Asp Ser Phe Lys Gly Gly Gly Arg Ile Val Gly Ala Trp
305                 310                 315                 320

Pro Leu Glu Asp Val Pro Leu Ser Arg Ser Gln Arg Ile Glu Leu Gln
                325                 330                 335

Arg Gln Leu Ala Ala Arg Gly His Asp Pro Gly Ala
                340                 345

<210> SEQ ID NO 34
<211> LENGTH: 325
<212> TYPE: PRT
<213> ORGANISM: Pseudomonas aeruginosa

<400> SEQUENCE: 34

Val Gln Trp Val Gly Val Ala Gly Val Ile Gly Leu Ser Gly Ala Ala
1               5                   10                  15

Gln Ala Gly Asp Tyr Asp Gly Ser Pro Gln Val Ala Glu Phe Val Ser
            20                  25                  30

Glu Met Thr Arg Asp Tyr Gly Phe Ala Gly Glu Gln Leu Met Gly Leu
        35                  40                  45

Phe Arg Asp Val Asn Arg Lys Gln Ser Ile Leu Asp Ala Ile Ser Arg
    50                  55                  60

Pro Ala Glu Arg Val Lys Gln Trp Lys Glu Tyr Arg Pro Ile Phe Ile
65                  70                  75                  80

Ser Asp Ala Arg Ile Ser Arg Gly Val Asp Phe Trp Asn Lys His Ala
                85                  90                  95

Glu Asp Leu Ala Arg Ala Glu Lys Glu Tyr Gly Val Pro Ala Glu Ile
            100                 105                 110

Ile Val Ser Ile Ile Gly Val Glu Thr Phe Phe Gly Arg Asn Thr Gly
        115                 120                 125

Ser Tyr Arg Val Met Asp Ala Leu Ser Thr Leu Gly Phe Asp Tyr Pro
    130                 135                 140

Pro Arg Ala Asp Phe Phe Arg Lys Glu Leu Arg Glu Phe Leu Leu Leu
145                 150                 155                 160

Ala Arg Glu Gln Gln Val Asp Pro Leu Ser Leu Thr Gly Ser Tyr Ala
                165                 170                 175

Gly Ala Met Gly Leu Pro Gln Phe Met Pro Ser Ser Phe Arg Ala Tyr
            180                 185                 190
```

```
Ala Val Asp Phe Asp Gly Asp Gly His Ile Asn Ile Trp Ser Asp Pro
        195                 200                 205

Thr Asp Ala Ile Gly Ser Val Ala Ser Tyr Phe Lys Gln His Gly Trp
    210                 215                 220

Val Thr Gly Glu Pro Val Val Ser Val Ala Glu Ile Asn Asp Glu Ser
225                 230                 235                 240

Ala Glu Ser Ala Val Thr Arg Gly Val Asp Pro Thr Met Ser Leu Gly
            245                 250                 255

Glu Leu Arg Ala Arg Gly Trp Arg Thr His Asp Ala Leu Arg Asp Asp
        260                 265                 270

Gln Lys Val Thr Ala Met Arg Phe Val Gly Asp Lys Gly Ile Glu Tyr
    275                 280                 285

Trp Val Gly Leu Pro Asn Phe Tyr Val Ile Thr Arg Tyr Asn Arg Ser
290                 295                 300

Ala Met Tyr Ala Met Ala Val Tyr Gln Leu Ala Gly Glu Ile Ala Arg
305                 310                 315                 320

Ala Arg Gly Ala His
            325

<210> SEQ ID NO 35
<211> LENGTH: 405
<212> TYPE: PRT
<213> ORGANISM: Pseudomonas aeruginosa

<400> SEQUENCE: 35

Met Arg Asn Pro Glu Arg Ser Ala Leu Leu Lys Val Ser Gly Leu Leu
1               5                   10                  15

Gly Ser Thr Val Val Ala Met Gly Leu Gly Leu Ser Ser Ala Cys Ala
            20                  25                  30

Gln Lys Asn Pro Thr Val Glu Tyr Asn Gln Pro Ala Ala Pro Leu Gln
        35                  40                  45

Thr Lys Ala Pro Phe Ser Gly Ala Gly Pro Ala Ala Ser Val Pro Ala
    50                  55                  60

Gly Ala Pro Asn Glu Ala Gln Pro Gly Gln Ser Phe Glu Gln Trp Arg
65                  70                  75                  80

Asp Ala Phe Arg Gln Gln Ala Leu Ala Gly Gly Ile Asp Ala Gln Thr
                85                  90                  95

Phe Asp Arg Ala Phe Ala Gly Val Gln Pro Asp Pro Ala Val Val Glu
            100                 105                 110

Ala Asp Arg Ser Gln Pro Glu Phe Thr Arg Pro Val Trp Lys Tyr Leu
        115                 120                 125

Glu Gly Ala Leu Asp Pro Leu Arg Val Arg Gln Gly Gln Ala Arg Leu
    130                 135                 140

Ala Gln His Ala Arg Ile Leu Gly Glu Val Asp Ala Arg Tyr Ala Val
145                 150                 155                 160

Asp Ala Asp Ala Val Val Ala Ile Trp Gly Met Glu Ser Asn Tyr Gly
                165                 170                 175

Ser His Met Gly Asn Lys Asn Val Ile Arg Ser Leu Ala Thr Leu Ala
            180                 185                 190

Tyr Glu Gly Arg Arg Pro Glu Phe Ala His Ala Gln Leu Leu Ala Ala
        195                 200                 205

Leu Lys Ile Leu Gln His Gly Asp Val Pro Ala Ser Phe Met Ile Gly
    210                 215                 220

Ser Trp Ala Gly Ala Met Gly Gln Thr Gln Phe Ile Pro Thr Thr His
225                 230                 235                 240
```

```
Asn Gln Tyr Ala Val Asp Phe Asp Gly Asp Gly Lys Arg Asp Ile Trp
            245                 250                 255

Gly Ser Pro Gly Asp Ala Leu Ala Ser Thr Ala Asn Tyr Leu Lys Ala
        260                 265                 270

Ser Gly Trp Ile Ala Gly Gln Pro Trp Gly Phe Glu Val Arg Leu Pro
        275                 280                 285

Ala Gly Phe Asp Tyr Ser Leu Ala Glu Leu Thr Ile Arg Lys Pro Leu
        290                 295                 300

Gly Glu Trp Gln Gly Met Gly Val Gln Gly Val Asn Gly Gly Pro Leu
305                 310                 315                 320

Pro Ser Gly Leu Ser Gly Glu Gln Ala Ser Leu Leu Pro Ala Gly
            325                 330                 335

His Arg Gly Pro Ala Phe Leu Val Leu His Asn Phe Arg Ala Ile Leu
                340                 345                 350

Lys Tyr Asn Asn Ser Ser Ala Tyr Ala Leu Ala Val Gly Leu Leu Ala
            355                 360                 365

Asp Ser Phe Lys Gly Gly Arg Ile Val Gly Ala Trp Pro Leu Glu
        370                 375                 380

Asp Val Pro Leu Ser Arg Ser Gln Arg Ile Glu Leu Gln Arg Gln Leu
385                 390                 395                 400

Ala Ala Arg Gly His
            405

<210> SEQ ID NO 36
<211> LENGTH: 367
<212> TYPE: PRT
<213> ORGANISM: Pseudomonas aeruginosa

<400> SEQUENCE: 36

Met Arg Arg Thr Ala Leu Ala Leu Pro Leu Phe Leu Leu Val Ser Ala
1               5                   10                  15

Cys Ser Ser Glu Pro Thr Pro Pro Lys Pro Ala Ala Lys Pro Gln
            20                  25                  30

Ala Arg Thr Val Ile Ser Pro Arg Pro Val Arg Gln Ser Val Gln Pro
            35                  40                  45

Ile Leu Pro Leu Arg Gly Asp Tyr Ala Asn Asn Pro Ala Ala Gln His
    50                  55                  60

Phe Ile Asp Arg Met Val Ser Gln His Gly Phe Asn Arg Gln Gln Leu
65                  70                  75                  80

His Asp Leu Phe Ala Gln Thr Gln Arg Leu Asp Trp Val Ile Arg Leu
                85                  90                  95

Met Asp Arg Gln Ala Pro Thr Tyr Thr Pro Pro Ser Gly Pro Asn Gly
            100                 105                 110

Ala Trp Leu Arg Tyr Arg Lys Lys Phe Val Thr Pro Gly Asn Val Gln
        115                 120                 125

Asn Gly Val Leu Phe Trp Asp Gln Tyr Glu Thr Asp Leu Gln Arg Ala
    130                 135                 140

Ser Arg Val Tyr Gly Val Pro Pro Glu Ile Ile Val Gly Ile Ile Gly
145                 150                 155                 160

Val Glu Thr Arg Trp Gly Arg Val Met Gly Lys Thr Arg Ile Ile Asp
                165                 170                 175

Ala Leu Ser Thr Leu Ser Phe Ser Tyr Pro Arg Arg Ala Glu Phe Phe
            180                 185                 190

Ser Gly Glu Leu Glu Gln Phe Leu Leu Gln Ala Arg Lys Glu Gly Thr
```

-continued

```
              195                 200                 205
Asp Pro Leu Ala Leu Arg Gly Ser Tyr Ala Gly Ala Met Gly Tyr Gly
        210                 215                 220

Gln Phe Met Pro Ser Ser Phe Thr Lys Tyr Ala Val Asp Phe Asp Gly
225                 230                 235                 240

Asp Gly His Ile Asp Leu Trp Asn Pro Arg Asp Ala Ile Gly Ser Val
                245                 250                 255

Ala Asn Tyr Phe Lys Gln His Gly Trp Val Ser Gly Asp Arg Val Ala
            260                 265                 270

Val Pro Ala Ser Gly Arg Ala Pro Ser Leu Glu Asp Gly Phe Lys Thr
        275                 280                 285

Leu Tyr Pro Leu Asp Val Leu Ala Ser Ala Gly Leu Arg Pro Gln Gly
        290                 295                 300

Pro Leu Gly Gly His Arg Gln Ala Ser Leu Leu Arg Leu Asp Met Gly
305                 310                 315                 320

Arg Asn Tyr Gln Tyr Trp Tyr Gly Leu Pro Asn Phe Tyr Val Ile Thr
                325                 330                 335

Arg Tyr Asn His Ser Thr His Tyr Ala Met Ala Val Trp Glu Leu Gly
            340                 345                 350

Lys Glu Val Asp Arg Val Arg His Arg Ser Val Val Arg Gln Asp
        355                 360                 365
```